(12) United States Patent
Distel et al.

(10) Patent No.: US 10,379,018 B2
(45) Date of Patent: Aug. 13, 2019

(54) APPARATUS AND METHOD FOR ISOLATING TARGET CELLS FROM A FLUID SAMPLE

(71) Applicant: Dana-Farber Cancer Institute, Inc., Boston, MA (US)

(72) Inventors: Robert J. Distel, Framingham, MA (US); Yvon E. Cayre, Paris (FR)

(73) Assignee: Dana-Farber Cancer Institute, Inc., Boston, MA (US)

( * ) Notice: Subject to any disclaimer, the term of this patent is extended or adjusted under 35 U.S.C. 154(b) by 201 days.

(21) Appl. No.: 15/533,613

(22) PCT Filed: Dec. 7, 2015

(86) PCT No.: PCT/US2015/064302
§ 371 (c)(1),
(2) Date: Jun. 6, 2017

(87) PCT Pub. No.: WO2016/094315
PCT Pub. Date: Jun. 16, 2016

(65) Prior Publication Data
US 2017/0336307 A1 Nov. 23, 2017

Related U.S. Application Data

(60) Provisional application No. 62/089,058, filed on Dec. 8, 2014.

(51) Int. Cl.
*G01N 1/40* (2006.01)
*C12M 1/12* (2006.01)
(Continued)

(52) U.S. Cl.
CPC ............ *G01N 1/4077* (2013.01); *B01L 3/502* (2013.01); *C12M 1/12* (2013.01); *C12M 3/06* (2013.01);
(Continued)

(58) Field of Classification Search
CPC ..... B01L 2200/0631; B01L 2300/0681; B01L 2300/0832; B01L 2300/087;
(Continued)

(56) References Cited

U.S. PATENT DOCUMENTS 7,887,572 B2 2/2011 Hossainy et al.
2009/0081772 A1 3/2009 Cayre
(Continued)

FOREIGN PATENT DOCUMENTS

CN 103881903 A 6/2014
EP 0253579 A1 1/1988
(Continued)

OTHER PUBLICATIONS

Desitter, I. et al., "A New Device for Rapid Isolation By Size and Characterization of Rare Circulating Tumor Cells," *Anticancer Research*, vol. 32 (Feb. 2011): 427-442.
(Continued)

*Primary Examiner* — John Kim
(74) *Attorney, Agent, or Firm* — Cooley LLP; Cynthia A. Kozakiewicz; Ivor R. Elrifi

(57) ABSTRACT

Systems, methods, and apparatus are disclosed for recovering one or more target cells from a fluid sample. A first chamber aligned with a first surface of a removable filter receives the fluid sample. The removable filter defines a plurality of pores configured to retain the one or more target cells on the first surface and/or in the plurality of pores, each pore of the plurality of pores having a first diameter smaller than a diameter of the one or more target cells in the first surface and a second diameter greater than the first diameter in a second surface of the removable filter. A second chamber comprises a hydrophilic microporous wick structure configured to contact the second surface of the remov-
(Continued)

able filter and capillarize any non-target cells and fluid from the fluid sample, drawing them into the second chamber.

32 Claims, 27 Drawing Sheets

(51) Int. Cl.
*G01N 33/49* (2006.01)
*B01L 3/00* (2006.01)
*G01N 1/28* (2006.01)
*C12M 3/06* (2006.01)
*C12M 1/00* (2006.01)

(52) U.S. Cl.
CPC ........... *C12M 47/04* (2013.01); *G01N 1/2813* (2013.01); *G01N 33/49* (2013.01); *B01L 3/5635* (2013.01); *B01L 2200/0631* (2013.01); *B01L 2300/0681* (2013.01); *B01L 2300/087* (2013.01); *B01L 2300/0832* (2013.01); *B01L 2300/0887* (2013.01); *B01L 2300/161* (2013.01); *B01L 2400/049* (2013.01); *B01L 2400/0481* (2013.01); *G01N 2001/4088* (2013.01)

(58) Field of Classification Search
CPC ....... B01L 2300/0887; B01L 2300/161; B01L 2400/0481; B01L 2400/049; B01L 3/502; B01L 3/5635; C12M 1/12; C12M 3/06; C12M 47/04; G01N 33/49; G01N 1/2813; G01N 1/4077; G01N 2001/4088
See application file for complete search history.

(56) References Cited

U.S. PATENT DOCUMENTS

| 2011/0070642 A1 | 3/2011 | Cayre |
| 2011/0104670 A1 | 5/2011 | Cayre |

FOREIGN PATENT DOCUMENTS

| WO | WO8505451 A1 | 12/1985 |
| WO | WO 2009/047436 A1 | 4/2009 |
| WO | WO 2009/106760 A2 | 9/2009 |
| WO | WO 2011/055091 A2 | 5/2011 |
| WO | WO 2013/036819 A1 | 3/2013 |
| WO | WO2013036819 A1 | 3/2013 |

OTHER PUBLICATIONS

Kim, E. H. et al., "Enrichment of Cancer Cells From Whole Blood Using A Microfabricated Porous Filter," *Analytical Biochemistry*, vol. 440 (Sep. 2013): 114-116.

Fuh, G. et al., "Rational Design of Potent Antagonists to the Human Growth Hormone Receptor," Science, 256:1677-1680 (1992).

Herrmann, I. et al., "Highly Efficient Elimination of Colorectal Tumor-Initiating Cells by an EpCAM/CD3-Bispecific Antibody Engaging Human T Cells," PLoS ONE 5(10):e13474 (2010); doi:10.1371/journal.pone.0013474, 10 pages.

Hudson, P. J. & Kortt, A. A., "High avidity scFv multimers; diabodies and triabodies," Journal of Immunological Methods, 231:177-189 (1999).

Huston, J. S. & George, A. J. T., "Engineered antibodies take center stage," Human Antibodies, 10:127-142 (2001).

Mahanta, S. et al., "A Minimal Fragment of MUC1 Mediates Growth of Cancer Cells," PLoS ONE 3(4):e2054 (2008); doi:10.1371/journal.pone.0002054, 12 pages.

Ogawa, M. et al., "Fluorophore-Quencher Based Activatable Targeted Optical Probes for Detecting in Vivo Cancer Metastases," Molecular Pharmaceutics, 6(2):386-395 (2009).

Poljak, R. J., "Production and structure of diabodies," Structure, 2(12):1121-1123 (1994).

Rui, H. et al., "JAK2 Activation and Cell Proliferation Induced by Antibody-Mediated Prolactin Receptor Dimerization," Endocrinology, 135(4):1299-1306 (1994).

Schneider, H. et al., "Homodimerization of Erythropoietin Receptor by a Bivalent Monoclonal Antibody Triggers Cell Proliferation and Differentiation of Erythroid Precursors," Blood, 89:473-482 (1997), 25 pages provided.

Spaargaren, M. et al., "Antibody-induced Dimerization Activates the Epidermal Growth Factor Receptor Tyrosine Kinase," The Journal of Biological Chemistry, 266(3):1733-1739 (1991).

Stocks, M. R., "Intrabodies: production and promise," Drug Discovery Today, 9(22):960-966 (2004).

Tang, Y. et al., "Microfluidic device with integrated microfilter of conical-shaped holes for high efficiency and high purity capture of circulating tumor cells," Scientific Reports, 4:6052 (2014); doi: 10.1038/srep06052, and Supplementary Data http://www.nature.com/srep/2014/140813/srep06052.html, 21 pages.

Wheeler, Y. Y. et al., "Intrabody and Intrakine Strategies for Molecular Therapy," Molecular Therapy, 8(3):355-366 (2003).

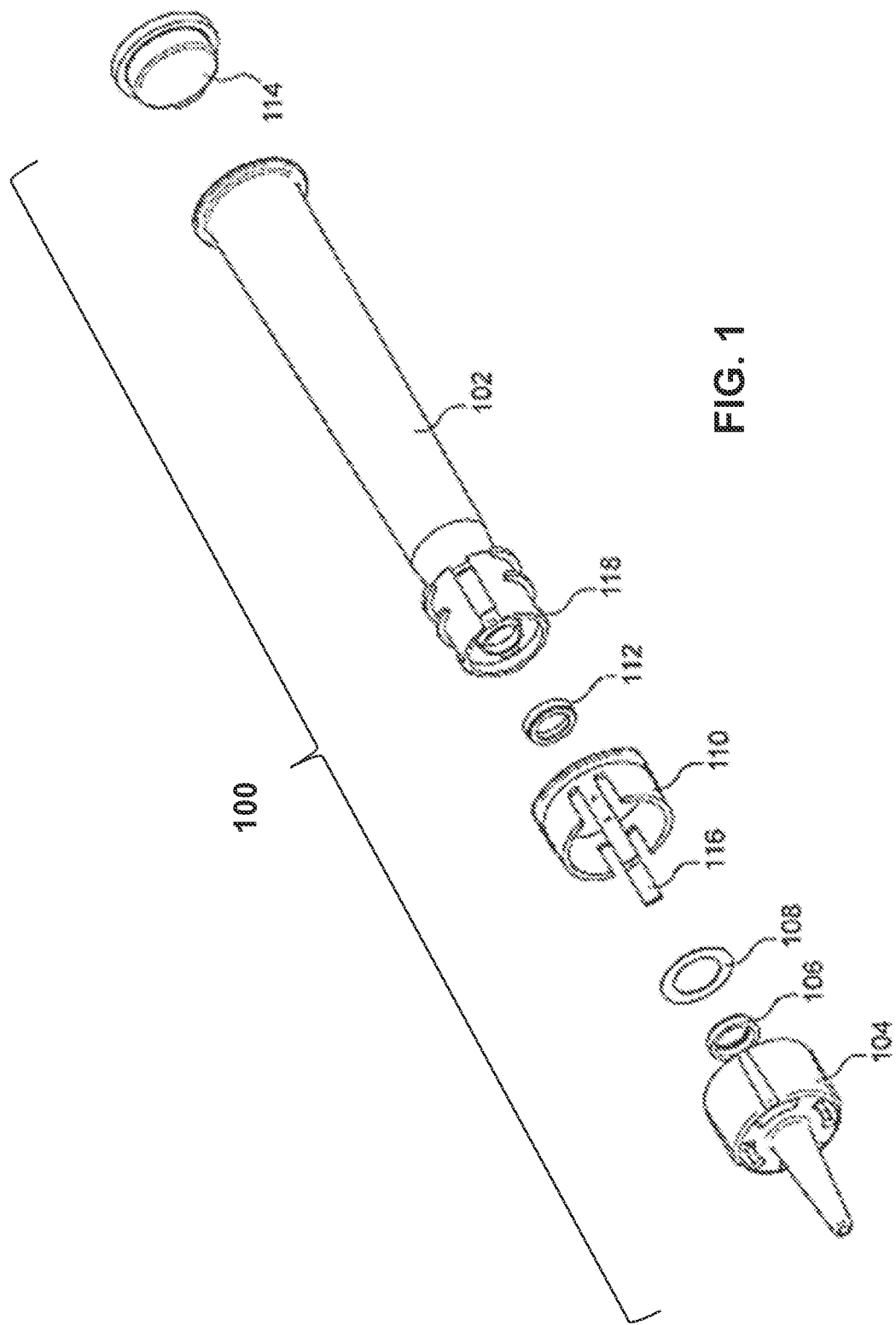

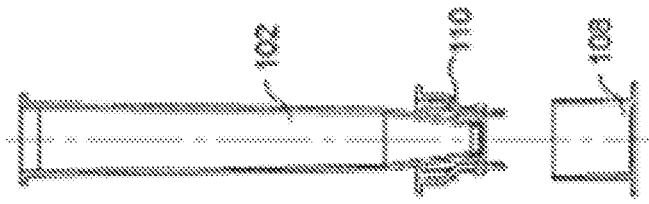
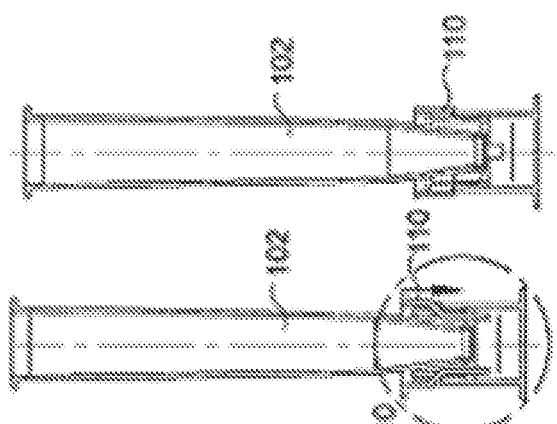
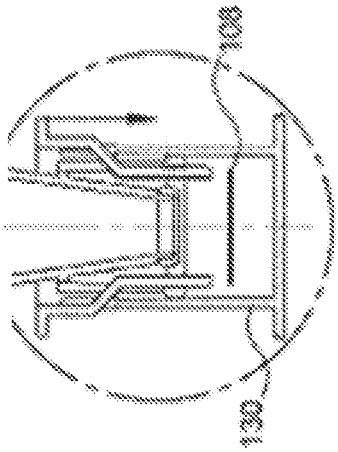
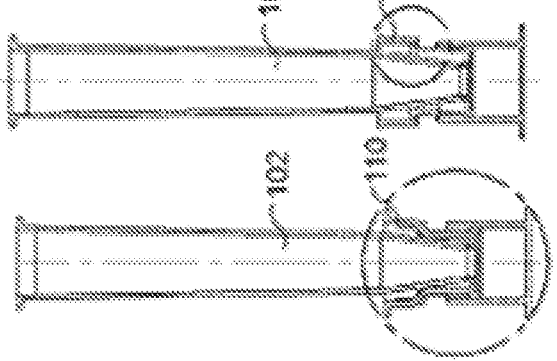
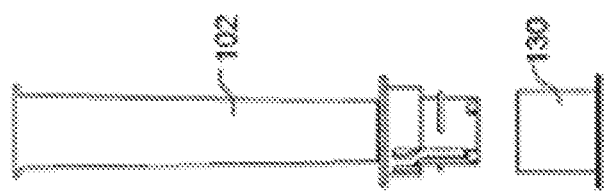
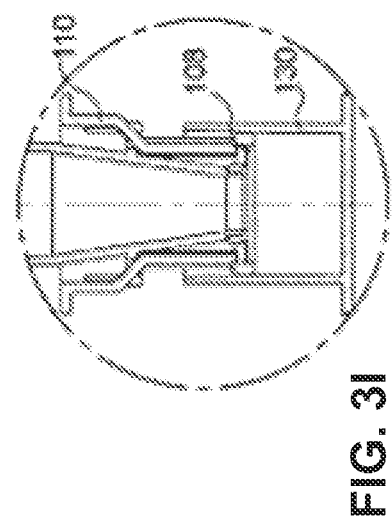

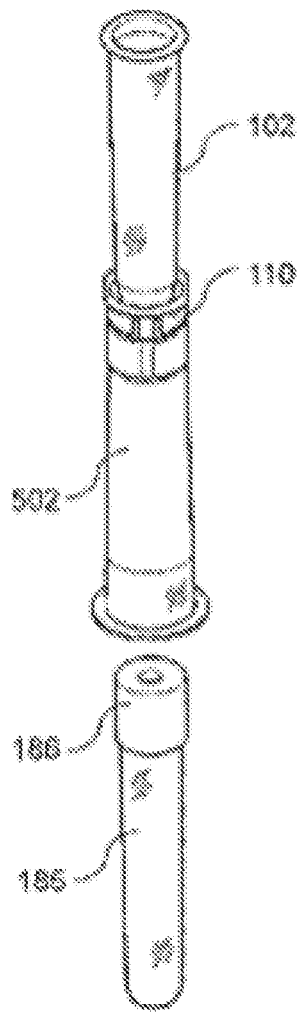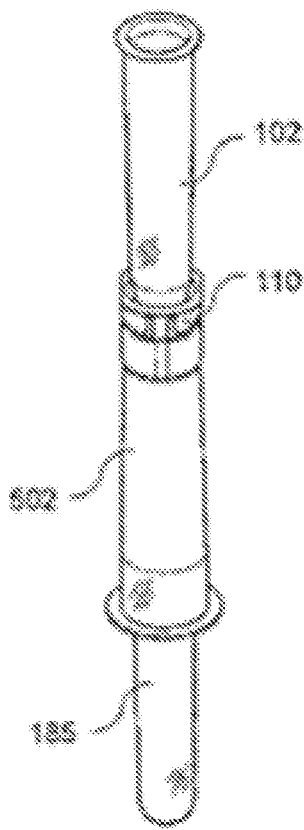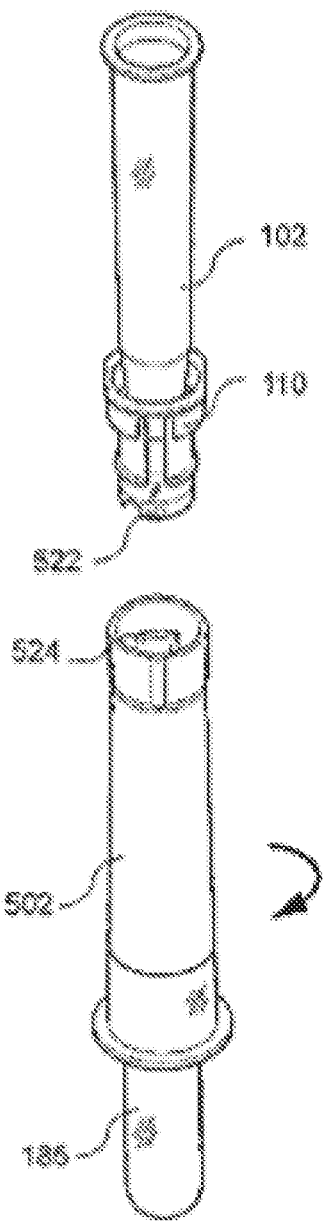
FIG. 5
FIG. 6
FIG. 7

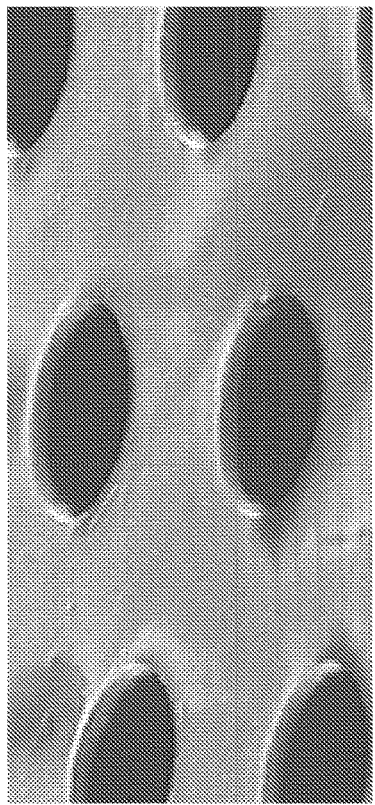
FIG. 18B
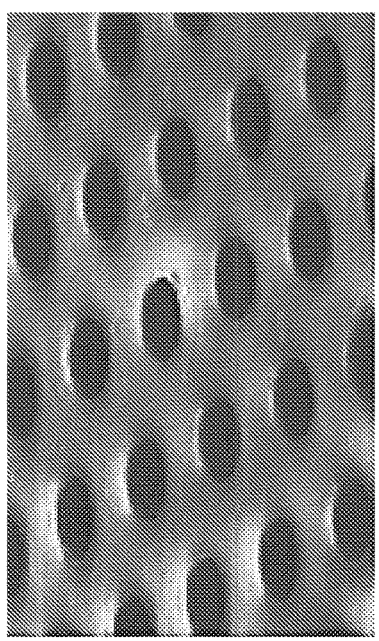
FIG. 18A
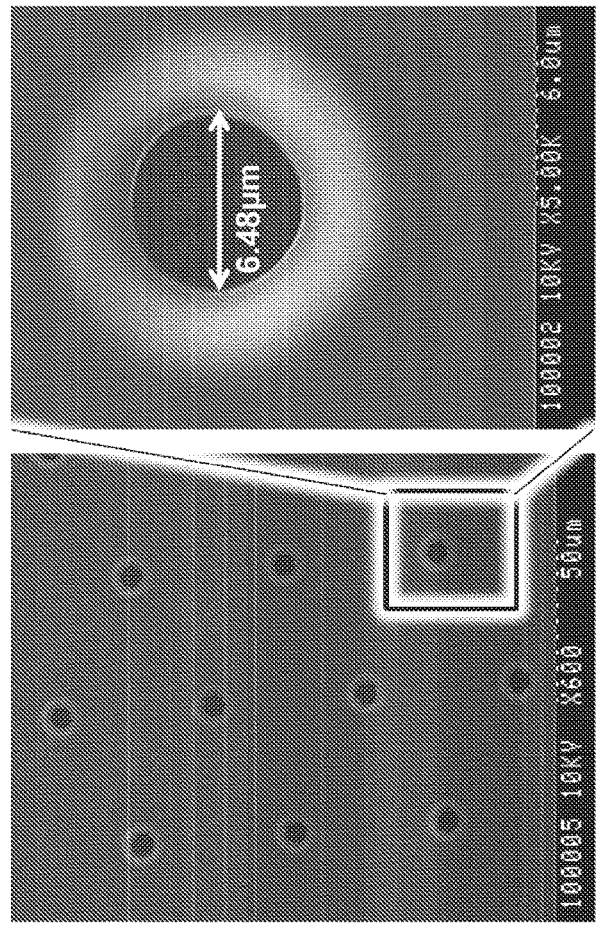
FIG. 18E
FIG. 18D
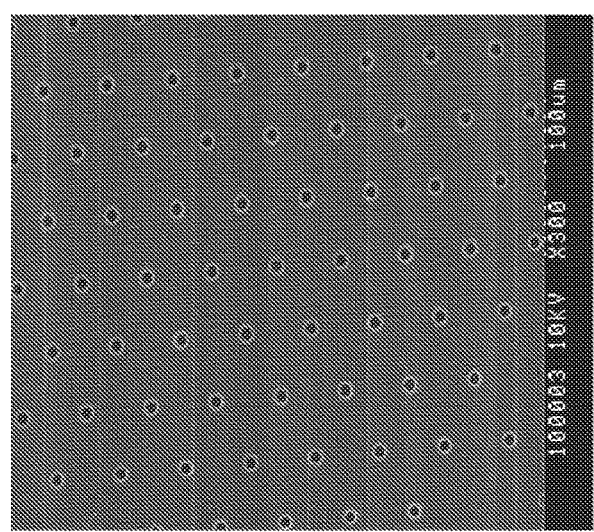
FIG. 18C

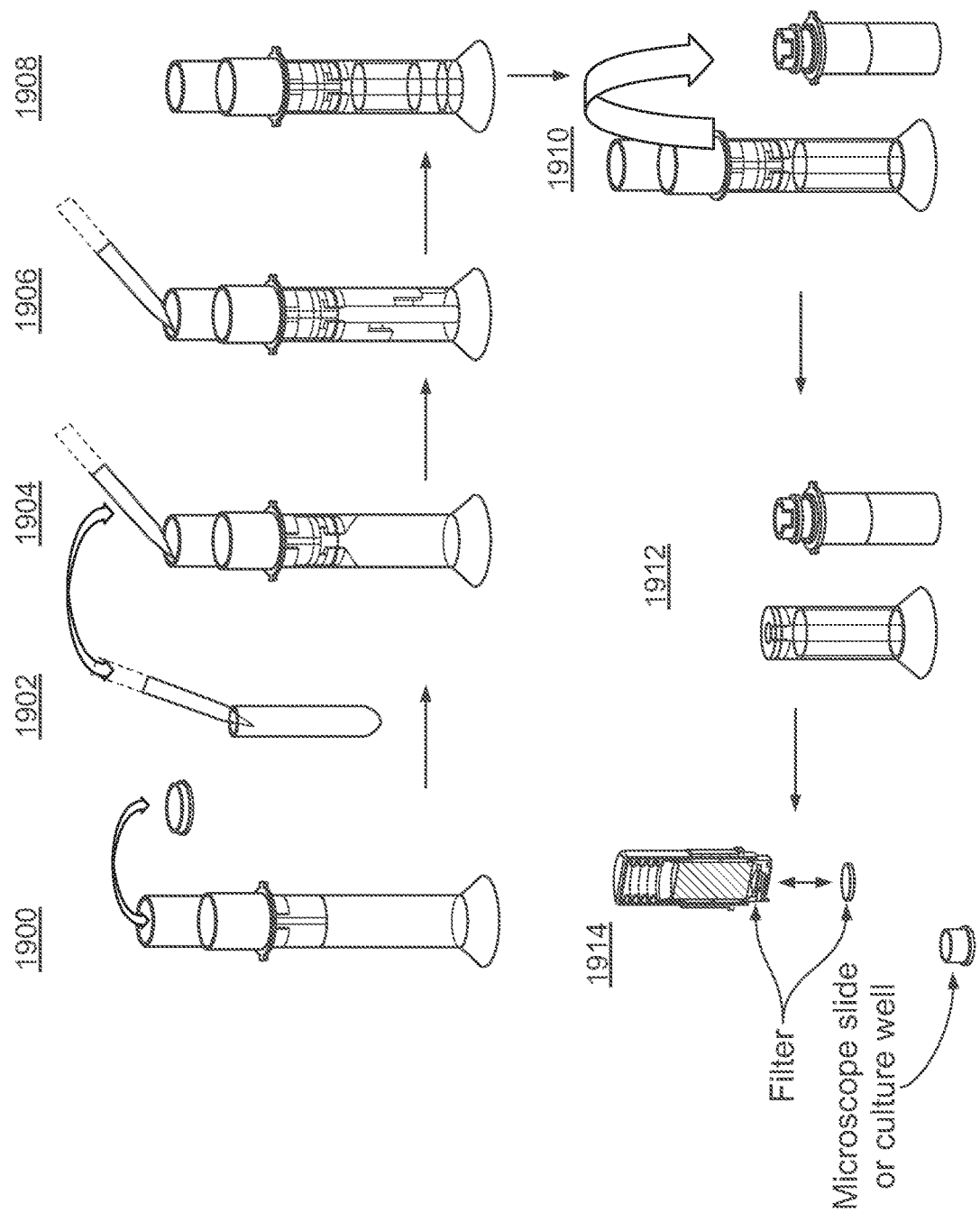

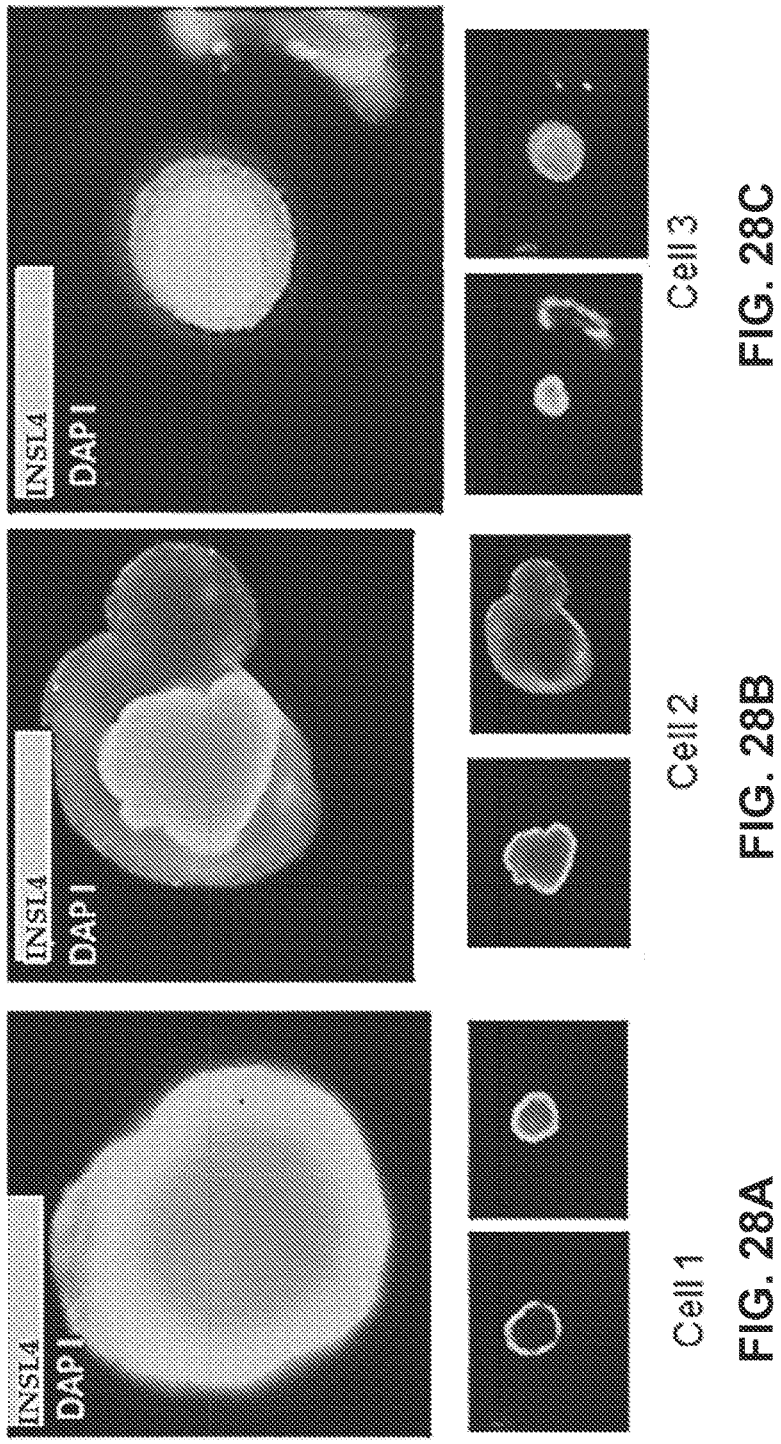
FIG. 28A Cell 1
FIG. 28B Cell 2
FIG. 28C Cell 3

APPARATUS AND METHOD FOR ISOLATING TARGET CELLS FROM A FLUID SAMPLE

CROSS-REFERENCE TO RELATED APPLICATIONS

This application is a national stage application filed under 35 U.S.C. § 371 of PCT/US15/64302 filed on Dec. 7, 2015 and claims priority to, and the benefit of U.S. Provisional Application No. 62/089,058 filed on Dec. 8, 2014, and the contents of which are incorporated herein by reference in their entireties.

TECHNICAL FIELD

The present disclosure relates to systems, methods, and apparatus for isolating cells from a fluid sample containing cells, and more particularly to increasing a number of target cells recovered from a fluid sample containing target cells and non-target cells and/or proliferating the recovered target cells.

BACKGROUND

Despite considerable progress in diagnosing and treating solid tumors, metastatic disease remains the foremost cause of cancer-related death. Although the mechanisms of metastasis development are yet to be fully elucidated, the circulation of tumor cells derived from the primary tumor in the bloodstream of a patient is a fundamental intermediate event in the metastatic cascade. Circulating tumor cells (CTCs) in peripheral blood of cancer patients can be reliable biomarkers for detection of, e.g., metastasis and earlier detection of secondary tumors as well as monitoring of, e.g., disease progression and/or response to therapy. Despite their high phenotype heterogeneity, it remains challenging to capture CTCs with high efficiency and high purity because such a relatively small number of CTCs are present in the blood (e.g., about 1 CTC per 10⁹ cells in peripheral blood of patients with metastatic cancer).

Size-based filtration allows for isolation of both epithelial and mesenchymal phenotypes, which are more appropriate for analyses of tumor heterogeneity, tumor drug resistance, etc. The main problem of this approach is contamination: the track-etched cylindrical holes of the filter have generally high retention ratio of non-tumor cells if the size of the holes is sufficiently small to reach high tumor cell capture efficiency.

SUMMARY

Applicants have recognized and appreciated that the rarity of some cells in a fluid, such as CTCs and fetal embryonic cells circulating in the blood, makes these cells particularly difficult to detect, isolate, and/or proliferate.

According to one embodiment, an apparatus for isolating one or more target cells from a fluid sample includes a first chamber for receiving the fluid sample with a first opening at the top of the first chamber and a second opening at the bottom of the first chamber. The first opening is configured to receive the fluid sample, and the second opening is configured to align with a removable filter. The removable filter has a first surface facing the interior of the first chamber and a second surface opposite the first surface. The removable filter defines a plurality of pores configured to retain the one or more target cells from the fluid sample on the first surface and/or in the plurality of pores and to pass any non-target cells and fluid from the fluid sample through the plurality of pores. Each pore of the plurality of pores has a first diameter in the first surface, the first diameter being smaller than a diameter of the one or more target cells, and a second diameter in the second surface, the second diameter being greater than the first diameter. A second chamber is in communication with the first chamber through the plurality of pores for receiving the any non-target cells and the fluid from the fluid sample. The second chamber includes a hydrophilic microporous wick structure configured to contact the removable filter and capillarize the any non-target cells and the fluid from the fluid sample such that the any non-target cells and the fluid from the fluid sample are drawn into the second chamber and the one or more target cells are isolated on the first surface of the removable filter.

International Publication No. WO 2013/036819, published Mar. 14, 2013, corresponding to International Patent Application No. PCT/US2012/054241, filed Sep. 7, 2012, and entitled, "Methods of Increasing the Number of Target Cells Recovered from a Fluid Sample," is hereby incorporated herein by reference in its entirety.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

Other systems, processes, and features will become apparent to those skilled in the art upon examination of the following drawings and detailed description. It is intended that all such additional systems, processes, and features be included within this description, be within the scope of the present invention, and be protected by the accompanying claims.

BRIEF DESCRIPTION OF THE DRAWINGS

The skilled artisan will understand that the figures, described herein, are for illustration purposes only, and that the drawings are not intended to limit the scope of the disclosed teachings in any way. In some instances, various aspects or features may be shown exaggerated or enlarged to facilitate an understanding of the inventive concepts disclosed herein (the drawings are not necessarily to scale, emphasis instead being placed upon illustrating the principles of the teachings). In the drawings, like reference characters generally refer to like features, functionally similar and/or structurally similar elements throughout the various figures.

FIG. 1 is an exploded perspective view of a filtration device for recovering target cells from a fluid sample, according to some embodiments.

FIG. 5 is a perspective view of the filtration device from FIG. 4, after removal of a protective film and before insertion of a vacuum tube, according to some embodiments.

FIG. 6 is a perspective view of the filtration device from FIG. 5, after insertion of the vacuum tube, according to some embodiments.

FIG. 7 is a perspective view of the filtration device from FIG. 6, during removal of the vacuum tube and a protective cylinder, according to some embodiments.

FIGS. 18A-18E are scanning microscopy images of filters with regular patterns of conical pores, in accordance with some embodiments.

FIG. 19 is a diagram illustrating a method of using a filtration device, according to some embodiments.

FIGS. 28A-28C are a series of fluorescence microscopy images fetal embryonic cells captured from a maternal blood sample, according to some embodiments of the present disclosure.

DETAILED DESCRIPTION

Figure 2D:
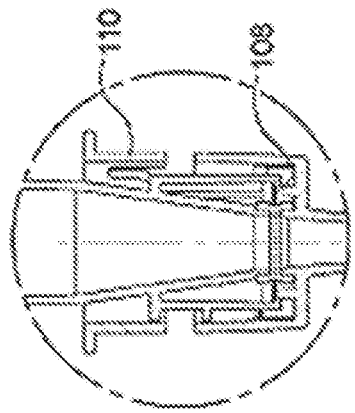
FIGS. 2A and 2C are cross-sectional views of the filtration device from FIG. 1, now assembled, according to some embodiments. The circled portions in FIGS. 2A and 2C are presented in enlarged view in FIGS. 2B and 2D, respectively.

Following below are more detailed descriptions of various concepts related to, and embodiments of, systems, methods and apparatus including target cell filtration features. It should be appreciated that various concepts introduced above and discussed in greater detail below may be implemented in any of numerous ways, as the disclosed concepts are not limited to any particular manner of implementation. Examples of specific implementations and applications are provided primarily for illustrative purposes.

In the present disclosure, the term "fluid sample containing cells" refers to a liquid containing a suspension of cells. Non-limiting examples include biological fluids such as blood (e.g., peripheral blood or umbilical cord blood), urine, lymph, cerebral spinal fluid, or ductal fluid, or such fluids diluted in a physiological solution (e.g., saline, phosphate-buffered saline (PBS), or tissue culture medium), or cells obtained from biological fluids (e.g., by centrifugation) and suspended in a physiological solution. Other examples of a "fluid sample containing cells" include cell suspensions (in physiological solutions) obtained from bone marrow aspirates, needle biopsy aspirates or biopsy specimens from, for example, lymph node or spleen. Such fluid samples can be obtained from any mammalian subject, including humans, monkeys, mice, rats, rabbits, guinea pigs, dogs, or cats. Fluid samples from human subjects may be particularly useful. In embodiments in which the fluid sample contains red blood cells (RBCs), the RBCs may be selectively lysed using, for example, a buffer containing ammonium chloride or saponin, or removed by, for example, density gradient sedimentation or hetastarch aggregation.

As described herein, viable target cells may be recovered from a fluid sample on or in a filter, which then may be analyzed (and/or implanted in an immunodeficient non-human animal, where the target cells can proliferate). Target cells may include, but are not limited to, fetal blood cells, circulating tumor cells (CTCs), disseminated tumor cells (DTCs) (i.e., tumor cells in bone marrow), or stem cells (e.g., cancer stem cells, mesenchymal stem cells, and/or endothelial stem cells). For example, fetal blood cells may be recovered from a sample of maternal blood (optionally diluted in a physiological solution) and used for non-invasive prenatal diagnosis. One or more filters containing target cells recovered from a subject having, or suspected of having, a cancer (e.g., breast cancer, ovarian cancer, colon cancer, lung cancer, pancreatic cancer, kidney cancer, liver cancer, prostate cancer, melanoma, bladder cancer, thyroid cancer, or lymphoma) may be characterized using one or more of genomic, proteomic, immunocytochemistry, or fluorescence in situ hybridization (FISH) assays, to, for example, aid in prognosis determination. The one or more filters also may be implanted in an immunodeficient non-human mammal to increase the number of target cells (including the progeny of target cells trapped in or on a filter) and/or support a determination of the capability of the target cells to initiate tumors, metastasize, and/or respond to one or more treatments (e.g., chemotherapeutic agents).

Non-target cells are all the cells other than the target cells in a fluid sample containing cells. For example, where the fluid sample containing cells is blood, in which the target cells are CTCs, non-target cells may include RBCs, lymphocytes (T and/or B), monocytes, and granulocytes, which are smaller than most cancer cells. In another example, where the fluid sample containing cells is a cell suspension prepared from lymph node tissue, in which the target cells are cancer cells, non-target cells may include lymphocytes (T and/or B), monocytes, macrophages, and granulocytes.

According to some embodiments, a fluid sample containing target and non-target cells is passed through a filtration device that includes a filter configured such that the target cells are retained on or in the pores in the filter. To prepare the sample for passage through the filtration device, the sample may be diluted with a buffer containing culture medium (e.g., RPMI media, such as RPMI 1640, DMEM, or MEM) supplemented with bovine serum albumin (BSA), a red blood cell lysis agent (e.g., ammonium chloride, saponin, or potassium bicarbonate), a biocidal agent (e.g., sodium azide or a hypochlorite solution (0.1 to 2 mM)), and/or a calcium channel blocker (e.g., amlodipine, benidipine, or barnidipine). For example, the buffer may be supplemented with about 0.2 g to about 2 g (e.g., 0.2, 0.3, 0.4, 0.5, 0.6, 0.7, 0.8. 0.9, 1.0, 1.2, 1.4, 1.6, 1.8, or 2.0 g) of BSA; about 0.01 g to about 0.1 g (e.g., 0.01, 0.02, 0.03, 0.04, 0.05, 0.06, 0.07, 0.08, 0.09, or 1.0 g) of an RBC lysis agent; about 0.1 mM to about 2 mM (e.g., 0.2, 0.3, 0.4, 0.5, 0.6, 0.7, 0.8. 0.9, 1.0, 1.2, 1.4, 1.6, 1.8, or 2.0 mM) of a biocidal agent; and/or about 5 nM to about 30 nM (e.g., 5, 10, 15, 20, 25, or 30 nM) of a calcium channel blocker. The diluted sample may be incubated for about one minute to about five minutes (e.g., one minute, two minutes, three minutes, four minutes, or five minutes). After incubation, a cell culture medium (e.g., RPMI) may be added to the diluted sample.

Filter Systems and Devices

The diluted sample is passed through a filtration device containing a filter, according to some embodiments. The filtration device is not limited to a particular structure and may be of any shape, size, and/or material as long as it is configured to (a) receive a fluid sample containing cells, (b) support a filter for retaining target cells, and (c) remove remaining fluid sample after passage through the filter.

In some embodiments, a filtration device includes a compartment for receiving a fluid sample and a filter mounted (e.g., removably) over and/or onto an opening of the compartment. In some embodiments, non-target cells of the sample are caused to pass through the filter by introducing a vacuum tube (e.g., a blood vacuum tube) inside the holder of the device which, once its rubber cap is pierced (e.g., by a needle), may establish a pressure difference between the compartment and the vacuum in the tube in order to aspirate the fluid through the filter and into the tube. The filtration device may include a needle mounted (e.g., removably) onto the opening of the compartment and configured to pierce the plug of the vacuum tube to create a negative pressure gradient (i.e., relative to ambient pressure) between the vacuum tube and the compartment.

In other embodiments, non-target cells of the sample are caused to pass through the filter by introducing a wick, such as a super- or hyper-hydrophilic wick. In some embodiments, a wick is vertically capillarized. By replacing the vacuum tube and/or pump with a wick, the filtration procedure is faster, the filtration device no longer requires a needle, and there is less risk of blood exposure.

During the passage of the sample through the filtration device, at least some non-target cells, if present, pass through the filter. In some embodiments, the majority (i.e., greater than 50%) to substantially all (i.e., greater than 99%) of the non-target cells present in the fluid sample pass through the filter. Non-target cells of the fluid sample may be drawn through the filter by the application of a wick or vacuum to the underside of the filter.

According to some embodiments, a filtration device is composed of one or more of the following: a plastic made of one or more polymers such as polycarbonate, polyamide, polyvinyl chloride, polypropylene, polyethylene, or a polyetheretherketone such as PEEK™; a metal alloy such as stainless steel (e.g., surgical steel); a ceramic; glass; or a composite material. See, for example, filtration devices described in U.S. Patent Publication No. 20110070642, U.S. Patent Publication No. 20110104670, U.S. Patent Publication No. 20090081772, U.S. Provisional Application No. 61/417,526, International Publication No. WO 2011/055091, International Publication No. WO 2009/106760, and International Publication No. WO 2009/047436, each of which is incorporated by reference in its entirety.

In some embodiments all or part(s) of a filtration device is designed to be reusable, disposable, and/or biodegradable.

FIG. 1 is an exploded perspective view of a filtration device 100 for recovering target cells from a fluid sample, according to some embodiments. In FIG. 1, the filtration device 100 includes a reservoir or compartment 102, an end-piece 104, a seal 106, a filter with its support 108, a movable member 110, a seal 112, and a plug 114.

Compartment 102 may be substantially cylindrical in shape. The upper end of compartment 102 may be sealed by plug 114 in such a way that it is impermeable. Movable member 110 may be substantially cylindrical in shape and may have two or more legs (e.g., two legs) 116 extending toward end-piece 104. The lower end of compartment 102 may have, on its external surface, discontinuous rings or lateral lugs 118 with gaps, the rings 118 guiding the body of the movable member 110 and the gaps guiding guide legs 116 of movable member 110.

The two or more legs (e.g., two legs) 116 of movable member 110, which extend toward end-piece 104, may angle and/or curve toward each other in this direction so that the separation between the ends of the legs 116 is of a distance less than the diameter of filter support 108. This particular shape allows movable member 110, after it is removed from end-piece 104, to apply pressure to filter support 108 so that the filter support may be released from compartment 102, along with its filter, while movable member 110 is being advanced toward filter support 108.

The ends of legs 116 of movable member 110 and the lower end of compartment 102 may be designed to be inserted into a cell culture box or well. For example, the diameter of the discontinuous ring at the end of compartment 102 may be designed so that compartment 102 can be supported on the edge of a cell culture box or well.

An end-piece or adaptor 104 may be located at the lower opening of compartment 102. End-piece 104 may grip the exterior wall of compartment 102. End-piece 104 may have a narrowing lower opening (i.e., opposite from compartment 102), which is smaller in diameter than the diameter of compartment 102, and which is sufficiently long to enable a leak-free mechanical fit of the aperture of a needle (described further below with respect to FIGS. 3B to 3D). End-piece 104 may be detachable, impermeable, and/or sterile.

In a manner coordinated with the shape of the lower end of compartment 102, which has lateral lugs 118, end-piece 104 may have rotation locking means for gripping the lugs. In this way, end-piece 104 may allow a filter support 108 to be held in place during filtration. End-piece 104 may also protect a filter from any splashes and/or potential contamination.

In some embodiments, compartment 102, end-piece 104, and/or movable member 110 is composed of one or more materials, such as polypropylene. Seals 106 and 112 may be composed of one or more materials, such as silicone.

When attached, the lower end of compartment 102 has an opening which discharges onto the filter held by filter support 108, which itself may be held in position by the lower end of compartment 102 and/or end-piece 104. According to some embodiments, a filter support and/or the filter itself is shaped as a ring-like disk. The filter may be micro-perforated and/or fused to a filter support (e.g., to the underside of filter support 108), such that the filter may be inserted into a filtration device along with the filter support. A filter support may be made of one or more materials including, but not limited to, plastics such as polyvinyl chloride (PVC) and/or metal alloys such as surgical steel. A filter support (e.g., the thickness and/or other dimensions thereof) may be designed to allow it to be scanned with the filter. For example, the external diameter of a filter support may be about 12 mm to about 13 mm (e.g., 12.6 mm), and the internal diameter of a filter support (which may correspond to the exposed surface of filter) may be about 5.5 mm to about 6.5 mm (e.g., 5.9 mm). In some embodiments, a filter support may include one or more identifiers such that filter and any cells collected therein and/or thereon may be associated with a subject, time-stamped, etc.

Figure 2B:
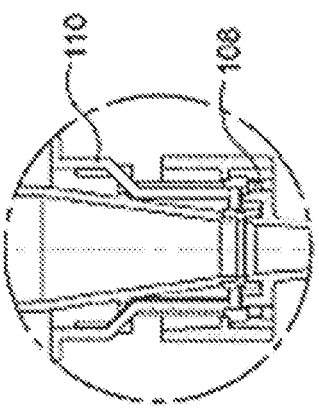
Figure 2C:
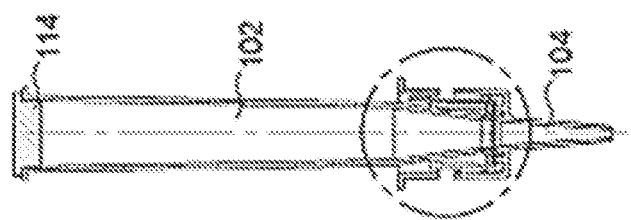
Figure 2A:
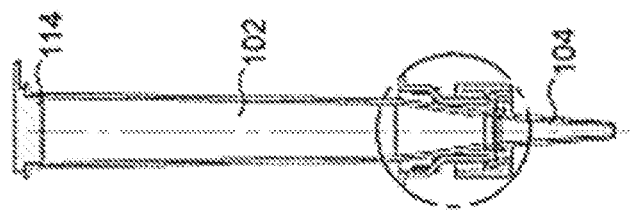

FIGS. 2A and 2C are cross-sectional views of perpendicular axial sections of the filtration device from FIG. 1, now assembled, according to some embodiments. The circled portion in FIG. 2A is presented in enlarged view in FIG. 2B, and the circled portion in FIG. 2C is presented in enlarged view in FIG. 2D. The circled portions illustrate the relationship between a movable member and filter support according to some embodiments. For example, the legs of movable member 110 angle toward each other so that the separation between the ends of the legs is smaller than the diameter of filter support 108, allowing movable member 110, after it is removed from end-piece 104, to apply pressure to filter support 108 so that the filter support may be released from compartment 102 while movable member 110 is being advanced toward filter support 108.

Figure 3A:
FIGS. 3A-3O are side, cross-sectional, and/or exploded views of the filtration device from FIG. 1, illustrating a method of using the device for isolating and/or recovering target cells from a fluid sample, according to some embodiments.

FIGS. 3A-3O are side, cross-sectional, and/or exploded views of the filtration device 100 from FIG. 1, illustrating a method of using the device for isolating and/or recovering target cells from a fluid sample, according to some embodiments.

Figure 3B:
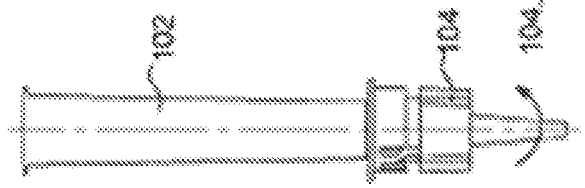

In FIG. 3A, the filtration device 100 is depicted in its storage configuration according to some embodiments. In FIG. 3B, a needle 180 with an aperture 181 is inserted into end-piece 104 according to some embodiments. Needle 180 may have a very fine, beveled end 182 to make it easier to pierce a vacuum tube plug. Aperture 181 of needle 180 may be made of plastic. At least end 182 of needle 180 may be made of metal. Needle 180 may be positioned on end-piece 104 either before or after the fluid sample is introduced into compartment 102 (e.g., through its upper opening) (not shown).

Figure 3C:
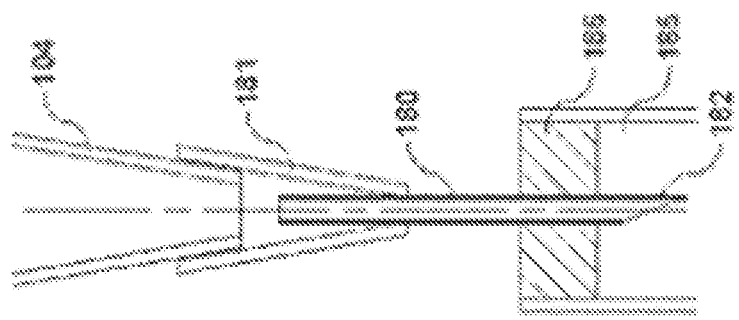
Figure 3D:
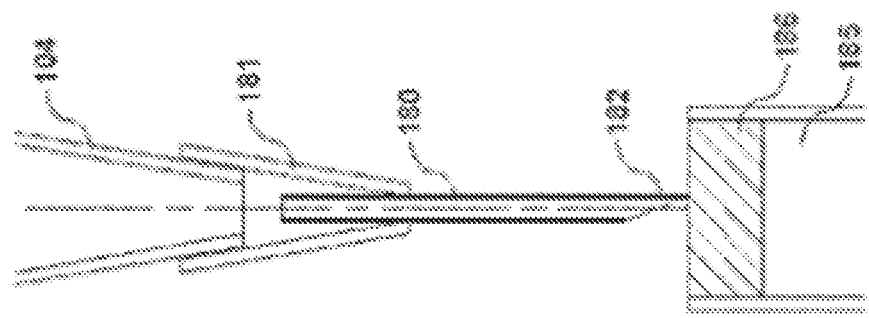

In FIG. 3C, a vacuum tube 185 with a plug 186 is positioned to be pierced by needle 180, which is impermeably joined to end-piece 104, according to some embodiments. In FIG. 3D, needle 180 completely pierces plug 186 to connect the interior of the negative pressure vacuum tube 185, through a filter, to the interior of compartment 102 holding the fluid sample according to some embodiments. The inner volume of the vacuum tube 185 may be greater than the volume of the liquid to be filtered. During filtration, any larger cells (particularly target cells) in the fluid sample in compartment 102, may be retained by a filter while substantially all of the fluid content and smaller are aspirated through the filter and into vacuum tube 185.

Figure 3E:
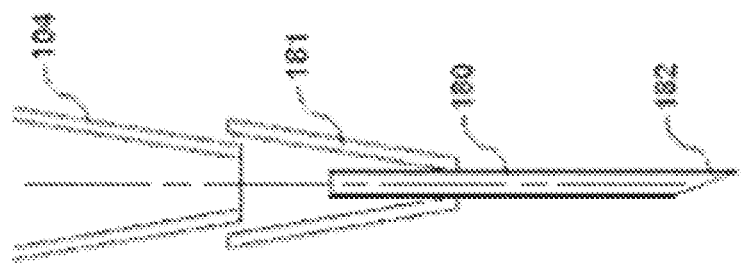
Figure 3F:
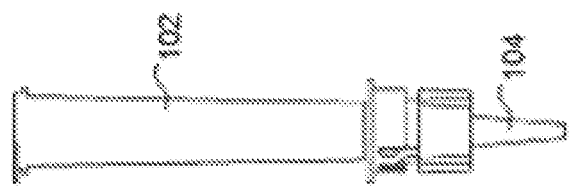

As illustrated in FIGS. 3E and 3F, end-piece 104 is rotated to release it from lugs 118 of compartment 102 and removed; and then, as illustrated in FIGS. 3G and 3H, the end of compartment 102 is inserted into a cell culture box or well 130, according to some embodiments.

As explained above and illustrated in FIG. 3I, the leg-end of movable member 110 and the lower end of compartment 102 may be designed to be inserted into a cell culture box or well 130, and the discontinuous rings 118 near the lower end of compartment 102 may have a diameter that allows compartment 102 to be supported on the edge of a culture box or well 130. To be more precise, as illustrated in FIGS. 3J and 3K, movable member 110 may still move parallel to the axis of compartment 102 according to some embodiments. During this movement (actuated by, e.g., an operator's fingers), as illustrated in FIGS. 3L, 3M, and 3N, one or more legs 116 of movable member 110 apply vertical downward pressure on a filter support 108 and release it from the lower end of compartment 102. The filter and its support 108 then fall into a cell culture box or well 130 in accordance with some embodiments. In FIG. 3O, compartment 102 and movable member 110 may be removed from the cell culture box or well 130.

According to some embodiments, either a wick or a vacuum tube/needle/etc. may be provided as a removable subsystem of the filtration device (housed in, e.g., a protective guiding cylinder). In some embodiments, the filter is supported by an alcove above a wick in a protective housing instead of in the lower end of the compartment.

FIGS. 4-7 are perspective views of the filtration device from FIG. 1, with a protective guiding cylinder 502 for a vacuum tube, according to some embodiments. Protective cylinder 502 may be attached to compartment 102 and/or movable member 110 using a multi-part connection.

Figure 4:
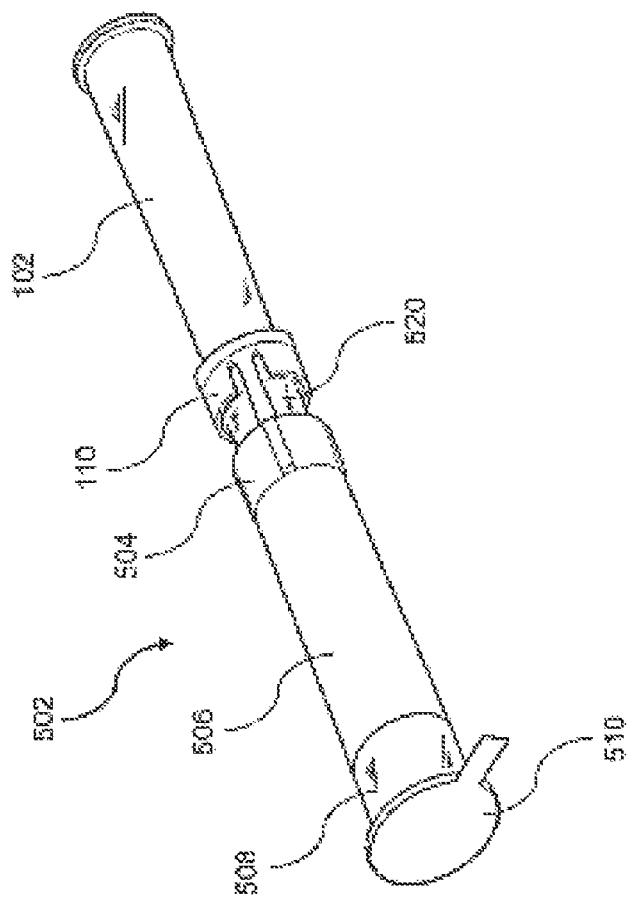
FIG. 4 is a perspective view of the filtration device from FIG. 1, prior to use, according to some embodiments.

FIG. 4 is a perspective view of the filtration device from FIG. 1, prior to use, according to some embodiments. Protective cylinder 502 may include a connection means part 504, a frosted part 506, a transparent part 508, and, on an opening opposite compartment 102, a protective film 510. In addition, part 520 (described further below with respect to FIG. 7) may be formed inside the end of compartment 102.

Protective cylinder 502 may be attached to end-piece 104 carrying needle 180 such that needle 180 is embedded in the lower part of connection means part 504, which faces compartment 102. Part 504 may be force-mounted onto frosted part 506 by means of spokes (e.g., four spokes). The spokes may be located on part 504 and inserted into four corresponding grooves located on frosted part 506, or vice versa. Frosted part 506 may be used to isolate and protect needle 180, whereas transparent part 508 may allow a user to visibly verify a status, such as completion of filtration.

Protective film 510 may be used to cover and/or seal the lower opening of protective cylinder 502. In some embodiments, protective film 510 includes a lateral part (e.g., a tab) extending a short distance from protective cylinder 502 for easier removal of film 510. Protective film 510 may protect a user from access to needle 180 as well as protect needle 180 from clogging and/or contamination.

Protective cylinder 502 may be distinctly colored (e.g., blue, green, yellow, etc.) to indicate the purpose(s) for which a filtration device is being used (e.g., cytology, molecular biology, culture study, etc.).

FIG. 5 is a perspective view of the filtration device from FIG. 4, after removal of protective film 510 and before insertion of vacuum tube 185 (or alternatively, a wick), according to some embodiments. After a fluid sample is introduced into compartment 102 and protective film 510 is removed, vacuum tube 185, fitted with its plug 186, may be inserted into protective guiding cylinder 502. Force then may be applied to vacuum tube 185 so that needle 180 pierces plug 186, as described above and illustrated in FIG. 6, which is a perspective view of the filtration device from FIG. 5, after insertion of the vacuum tube, according to some embodiments. In FIG. 6, the negative pressure initially present in vacuum tube 185 results in filtration of the fluid (and smaller cells) present in compartment 102.

When filtration is completed, as illustrated in FIG. 7, protective cylinder 502 is removed, according to some embodiments.

FIG. 7 also shows a particular embodiment of part 520, formed inside the end of compartment 102, comprising four prongs 522 laterally positioned on a cylindrical part in co-axial relation to compartment 102. In this embodiment, four grooves 524, with profiles corresponding to those of the prongs 522, extend in an elliptical fashion, from an opening designed to accommodate a prong 522 toward the interior of protective cylinder 502 such that, by rotating protective cylinder 502 as indicated by the arrow in FIG. 7, each prong 522 advances into the corresponding groove 524 and protective cylinder 502 is tightened onto compartment 102.

Figure 8:
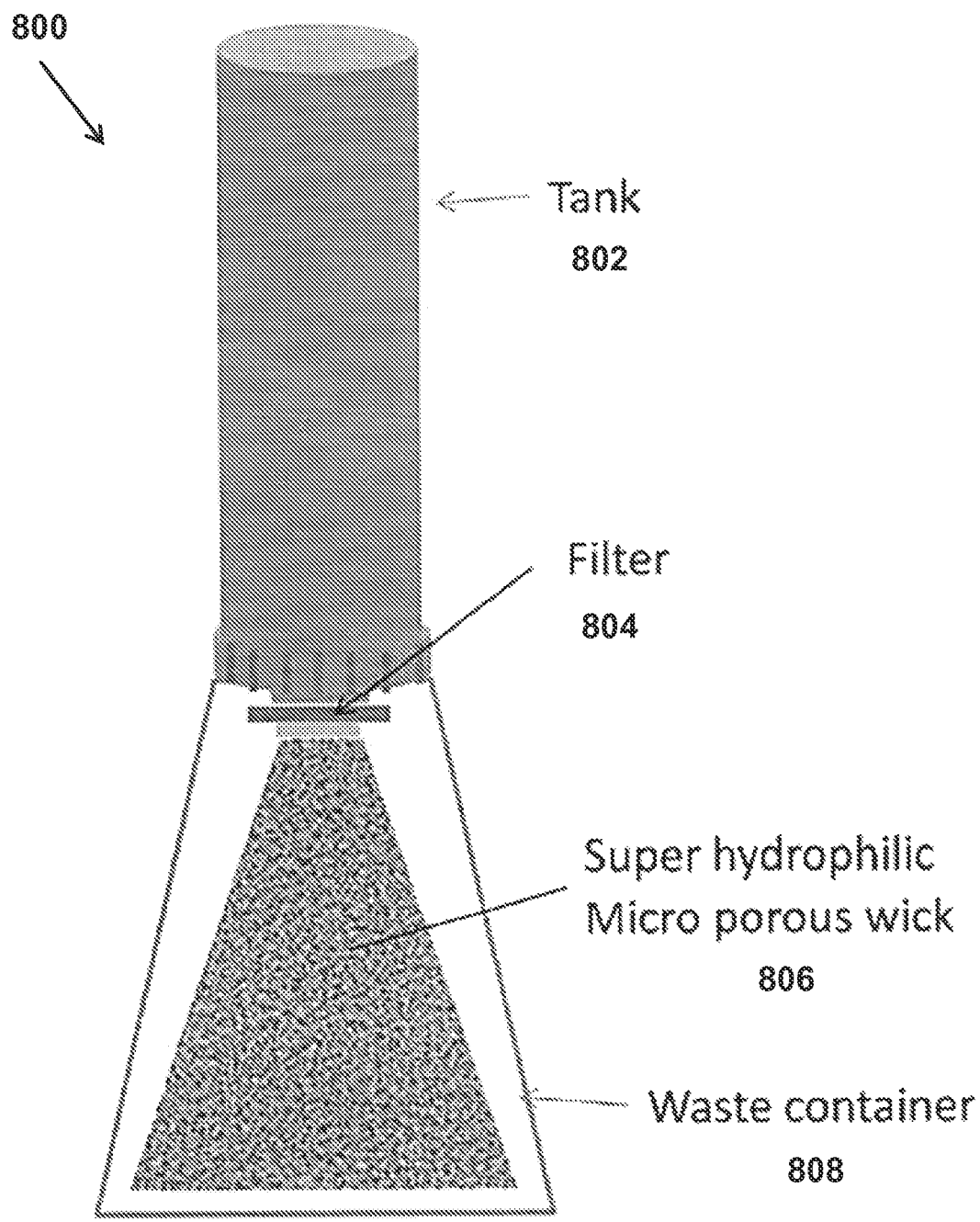
FIG. 8 is diagram of a filtration device for recovering target cells from a fluid sample, according to some embodiments.

FIG. 8 is diagram of a filtration device 800 for recovering target cells from a fluid sample, according to some embodiments. In FIG. 8, filtration device 800 includes a first compartment or tank 802 for receiving and/or holding the sample to be tested, a polymer or glass membrane or filter 804 with asymmetric pores for separating target cells from the fluid and other cells in the sample, a wick for pulling the fluid and other cells in the sample across the membrane/filter, and a second compartment/tank for receiving and containing waste (i.e., the fluid and other cells eliminated from in the sample through the filter/membrane).

The wick may comprise a microporous material (available from, e.g., Porex Corporation (Fairburn, Ga.)). The wick may be designed to efficiently wick the sample fluid, such as blood. The wick may be machined into a protective container (e.g., a cylinder) that can accommodate a volume commensurate with and/or specified by the volume of the first compartment or tank where a sample is introduced. A larger wick may be used to increase the volume of liquid. The protective container may be the same as or in addition to the second compartment/tank for receiving and containing waste. After use of the filtration device, waste (e.g., blood to be disposed) may be contained in the wick, thereby preventing exposure of a user to waste.

According to some embodiments, the bottom of a wick container (e.g., the second compartment/tank) may have a removable seal. For example, the bottom of a wick cylinder may be sealed with a screw cap. When fully sealed, the screw cap may force the wick against the top of the cylinder such that the filter is in contact, for example, tight contact with the wick. The top of a wick container (e.g., the second compartment/tank) may have an opening to expose the top of the wick. The opening may be machined to receive a particular filter shape and/or size. For example, the top of wick cylinder may have a small circular opening machined to fit a circular filter (e.g., a disc with a diameter of about 13 mm, in which the filter pores occupy a circular area with a diameter of about 9 mm in the center of the disc). When inserted, the filter may lay flat on top of the wick and/or fill the opening in the top of the wick container.

The first compartment/tank may have a corresponding opening of a similar size to allow fluid from the first compartment/tank to flow through the filter and into the second compartment/tank by gravity. Also, the microporous wick may generate and draw the fluid through the filter by capillary forces. The speed with which a fluid is drawn across the filter may be varied by modifying the surface characteristics of the microporous capillary network. The first compartment/tank may be coupled with and/or secured to the second compartment/tank in a number of ways including, but not limited to, a screw mechanism and a clip. In some embodiments, silicon and/or other materials may be used to form a water-tight seal between the top compartment/tank and the second compartment/tank. For example, a silicon ring may be attached to the opening in the bottom of the first compartment/tank and/or the opening in the top of the second compartment/tank to prevent fluid from escaping around the filter.

The flow of fluid from the top compartment/tank through the filter into the wick constitutes an in-line filter. However, the filter contains "dead areas" (i.e., areas between the pores). Thus, in some embodiments, the filter is designed to have a lateral flow component. For example, a vortex generator may be introduced above the filter. A vortex generator may include semicircular blades angled such that fluid passing through them creates a laminar flow across the filter membrane. The amount of laminar flow may be adjusted by modifying the angle of the blades and calibrated to sweep cells off the dead areas without disturbing target cells captured by the filter.

Figure 9:
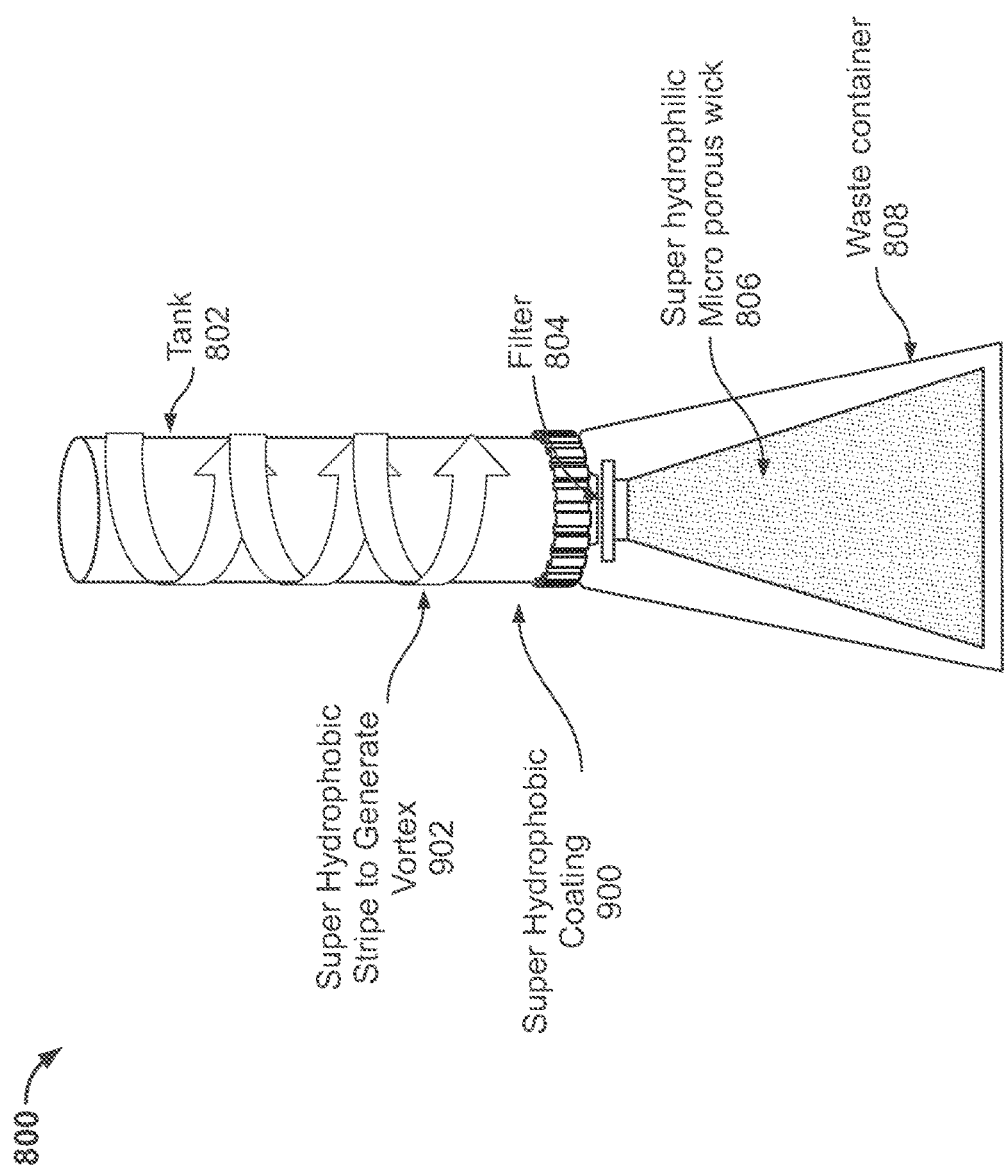
FIG. 9 is diagram of the filtration device from FIG. 8, in which the inner surface of the tank comprises a super-hydrophilic material and a spiral of super-hydrophobic material, according to some embodiments.

Some embodiments take advantage of super-hydrophilic and super-hydrophobic materials to increase the filtration rate and/or decrease the amount of contamination in the filtration device. For example, FIG. 9 is diagram of the filtration device 800 from FIG. 8, in which the inner surface of the tank 802 has been formed of and/or coated with a super-hydrophilic material 900 and a spiral ribbon of super-hydrophobic material 902, according to some embodiments. Fluid moving down the inner surface of the tank 802 will follow the contours of the hydrophobic spiral to create a vortex.

In some embodiments, the microporous wick is super-hydrophilic (e.g., comprising a POREX® material available from Porex Corp. (Fairburn, Ga.)). The inner surface of one or more pores and/or the lower surface of the filter may be treated and/or coated with one or more super-hydrophilic material, such as titanium dioxide. For samples comprising blood, a wick with super-hydrophilic characteristics also may prevent activation of clotting pathways and reduce the risk that blood will clot in the wick.

Figure 10C:
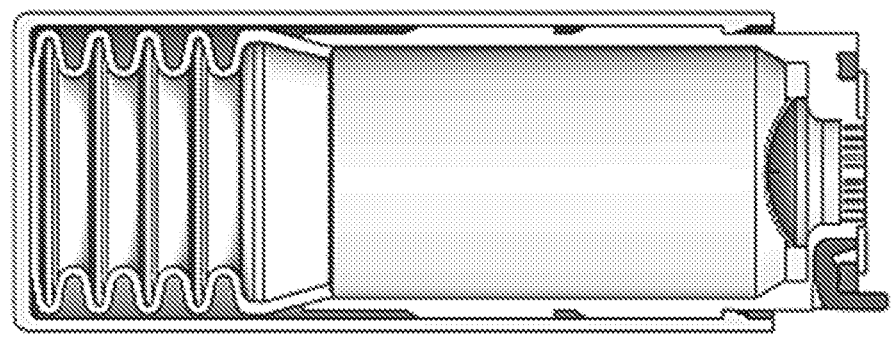
FIGS. 10A-10C illustrate different views of a filtration device for recovering target cells from a fluid sample, according to some embodiments.
Figure 10B:
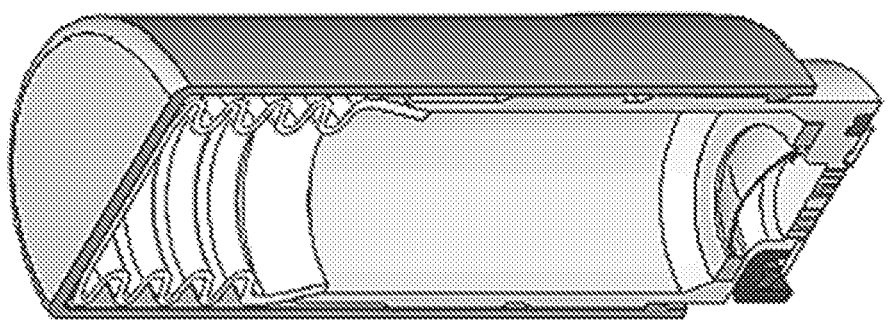
Figure 10A:
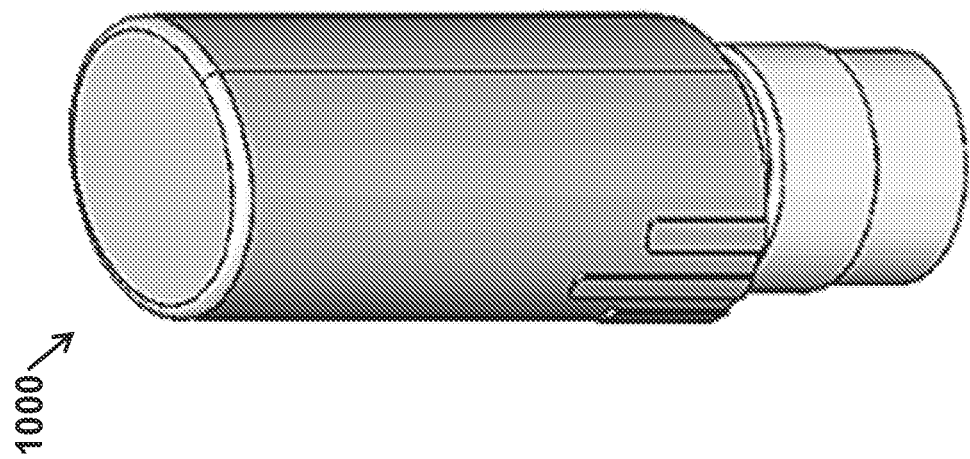
Figure 11A:
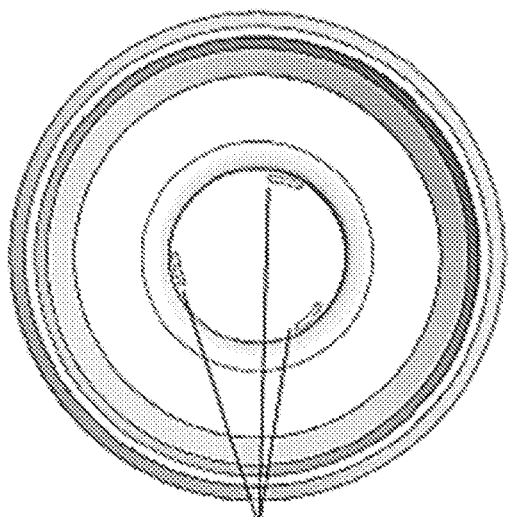
FIGS. 11A-11B illustrate top and bottom views of a portion of the filtration device from FIGS. 10A-10C, according to some embodiments.
Figure 11B:
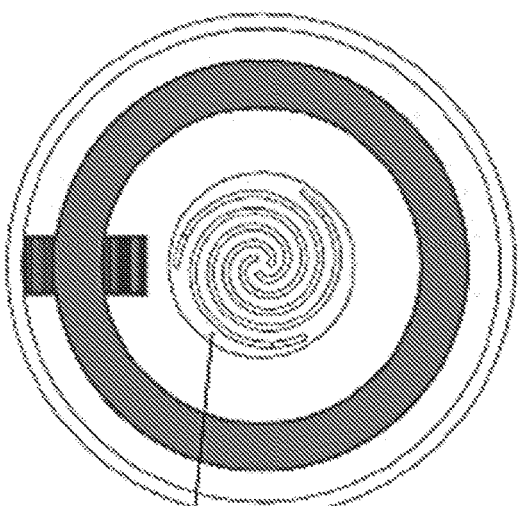
Figure 12:
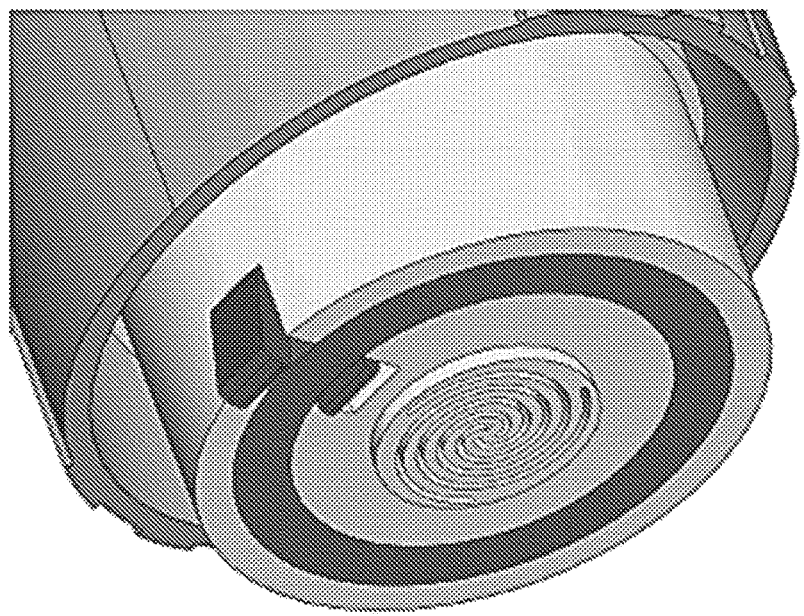
FIG. 12 is a perspective view of a spiral structure in the filtration device from FIGS. 11A-11B, according to some embodiments.

FIGS. 10A-10C illustrate different views of a filtration device 1000 for recovering target cells from a fluid sample, according to some embodiments. FIG. 10A is a perspective view, FIG. 10B is a perspective cross-sectional view, and FIG. 10C. is a cross-sectional view of the filtration device 1000. FIGS. 11A-11B illustrate top and bottom view, respectively. In FIG. 11A, three fluid entry points are noted, whereas, in FIG. 11B, a structure supporting spiral blood flow is diagramed. A perspective view of the spiral structure is shown in FIG. 12.

Filters

According to some embodiments, a filter is integrated in a device to allow fluid, red blood cells (RBCs), peripheral blood mononuclear cells (PBMCs), and other smaller cells to pass through one or more pores of the filter while preventing passage of any larger CTCs. RBCs and PBMCs that remain in the pores of a filter may make it difficult to interpret results when staining the filter directly. Likewise, damage to cells passing through the filter may set off clotting which can affect sample quality.

Figure 15:
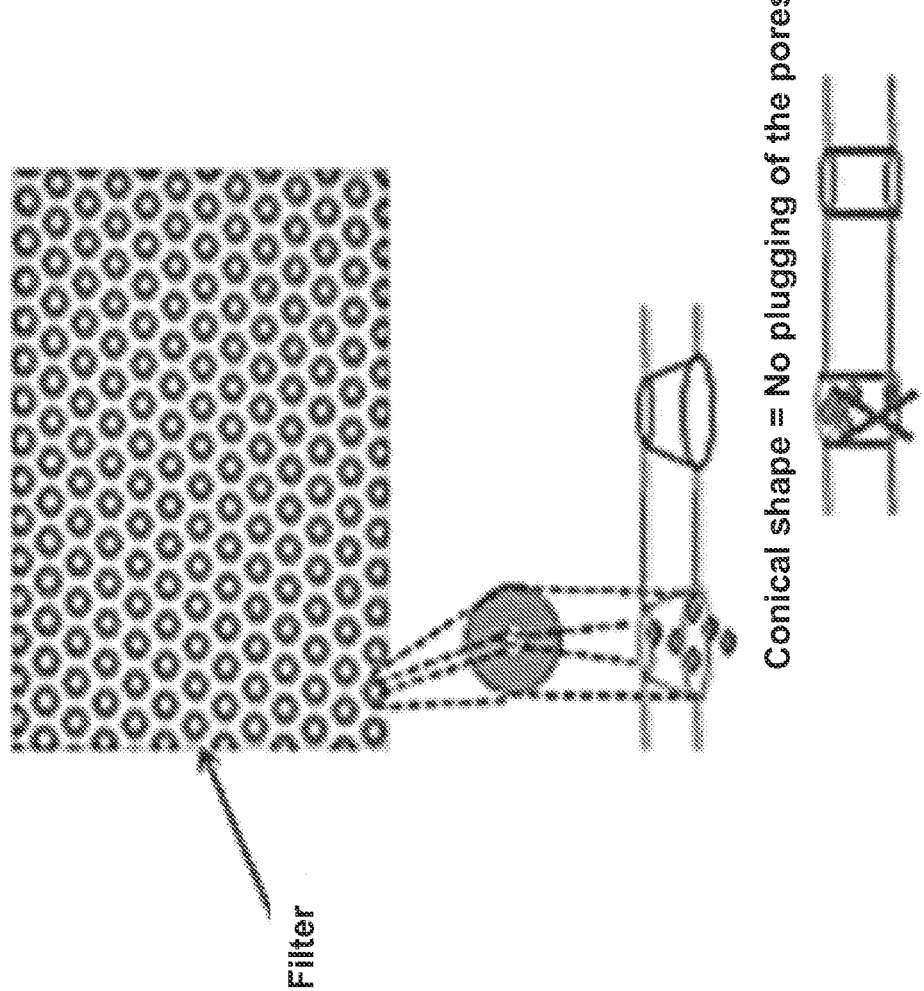
FIG. 15 is a diagram illustrating the advantages of a conical pore over a cylindrical pore, according to some embodiments.

FIGS. 13A-13D are sequential images of a filter with cylindrical pores and cells moving through the filter from left to right according to some embodiments. FIGS. 14A-14D are sequential images of a filter with conical pores and cells moving through the filter from left to right according to some embodiments. As diagramed in FIG. 15, conical pore may have several advantages over a cylindrical pore including, but not limited to, reducing the number of non-target cells that can become lodged in the pore, reducing damage to non-target cells as they pass through the pore, and increasing the surface of the pore to effectively increase the capillary action of the pore to draw the fluid and non-target cells across the filter with little or no exogenous force.

Figure 13:
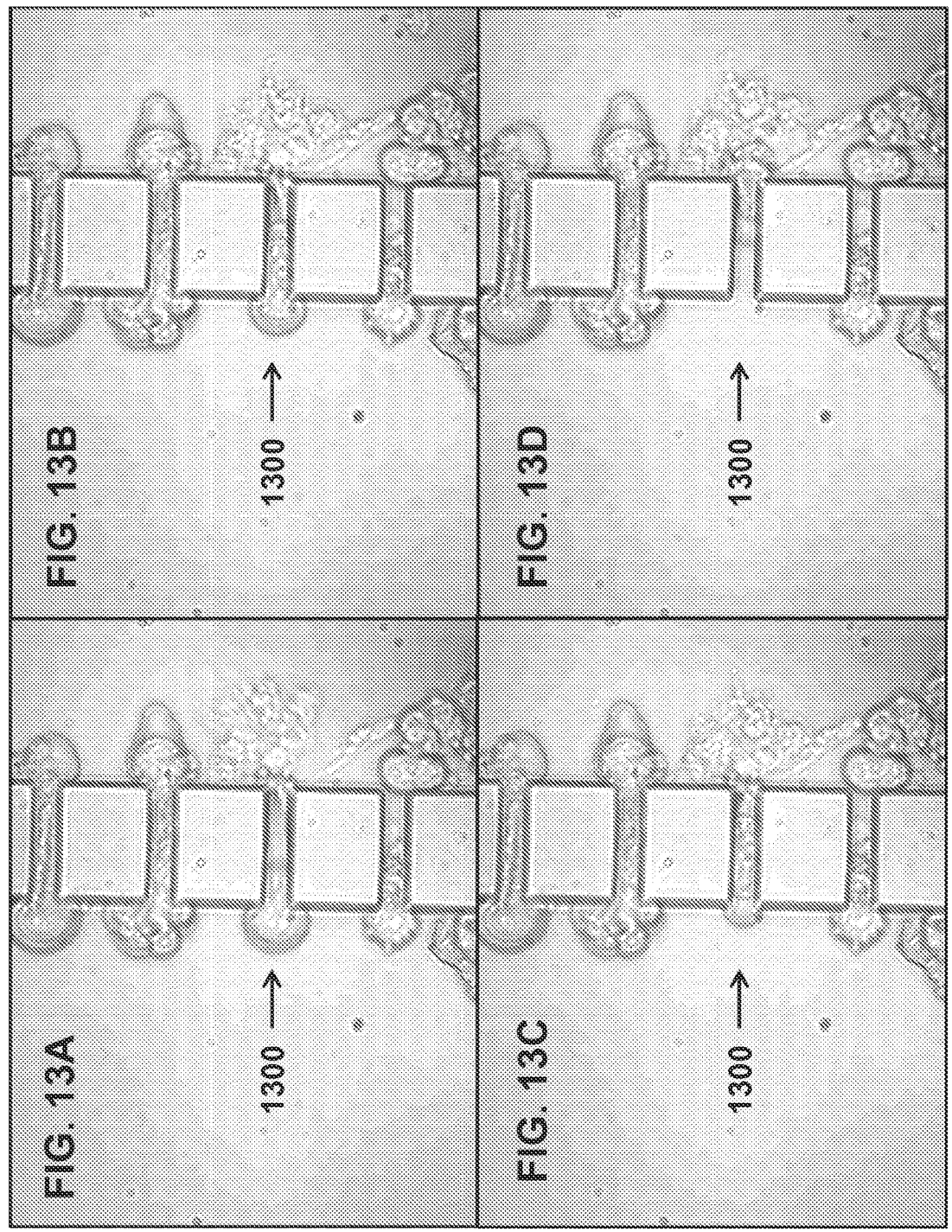
FIGS. 13A-13D are sequential photomicrographs of a filter with cylindrical pores and cells moving through the filter from left to right, according to some embodiments.
Figure 14:
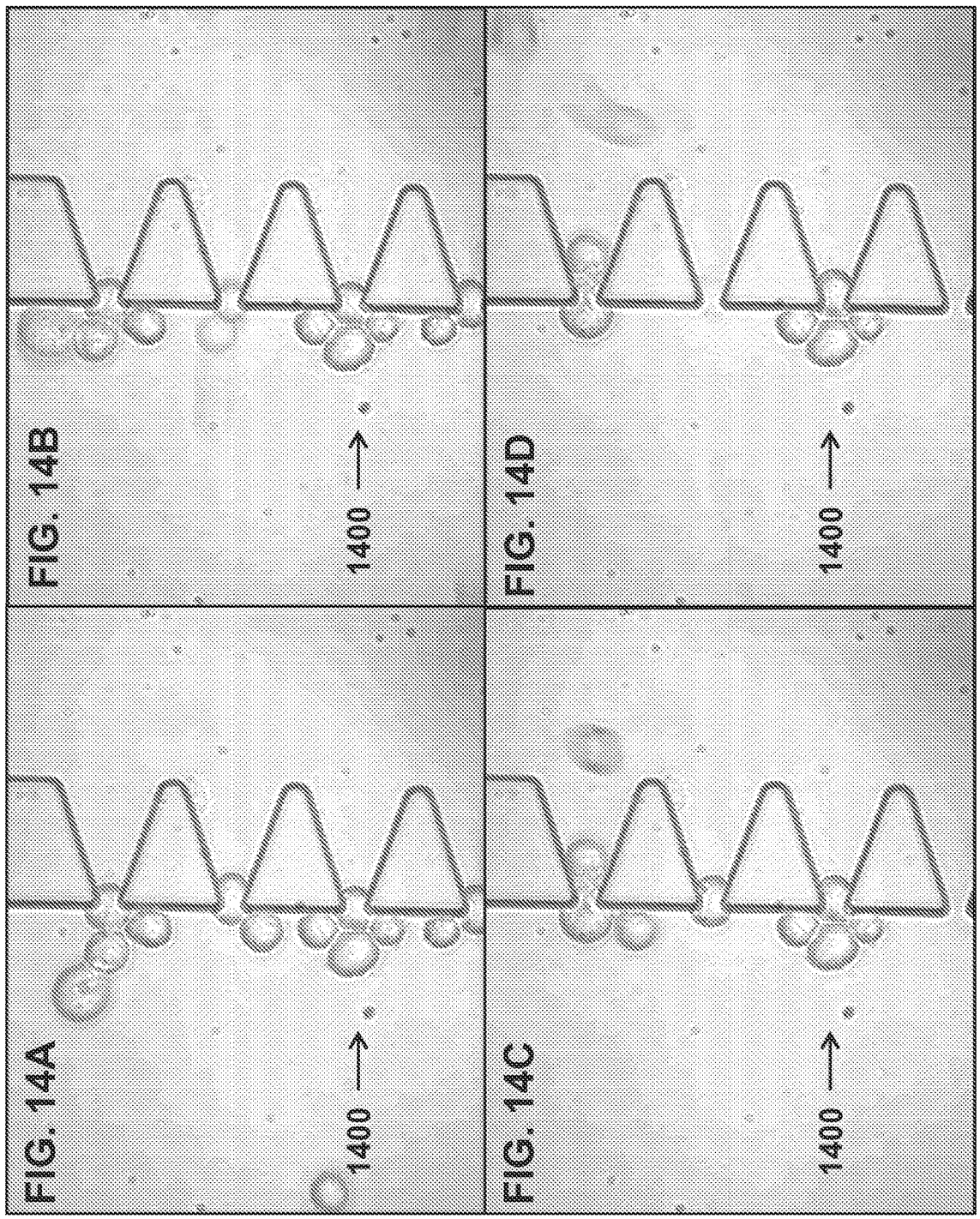
FIGS. 14A-14D are sequential photomicrographs of a filter with conical pores and cells moving through the filter from left to right, according to some embodiments.

For example, in FIGS. 13A-13D, three of the four cylindrical pores visible in the filter appear to be full of immobilized cellular material (perhaps clotted). In FIG. 13A, a cell is entering remaining pore 1300. In FIGS. 13B-13C, more and more of the cell is being squeezed within pore 1300 and the structure of the cell is disappearing. In FIG. 13D, cellular material is leaving pore 1300, but the cell's structure appears to be compromised and cellular debris continues to collect where the cellular material is exiting pore 1300.

On the other hand, in FIGS. 14A-14D, only one pore 1400 of the four conical pores visible in the filter appears to be blocked, and even then, only the entrance to the pore (i.e., the pore itself is not clogged with cellular material). Also note that the structure of the cells appear to stay the same when they exit the pores, and that, unlike FIGS. 13A-13D, no cellular debris or clotting is visible in FIGS. 14A-14D.

Figure 16:
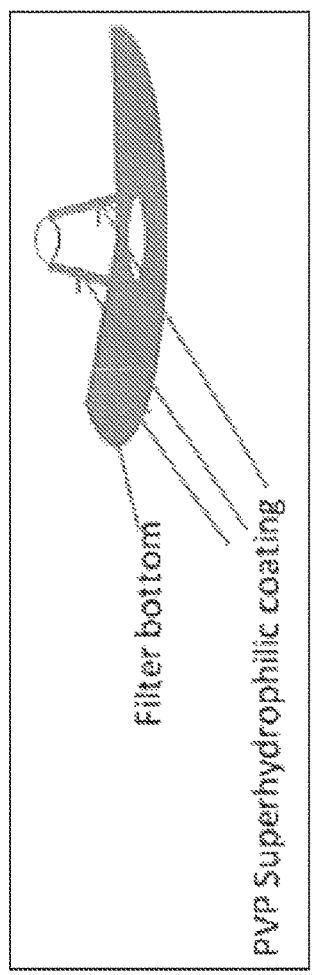
FIG. 16 is a diagram illustrating the coating of the inside surface of one or more pores and/or the bottom surface of a filter with a super-hydrophilic substance, according to some embodiments.
Figure 17:
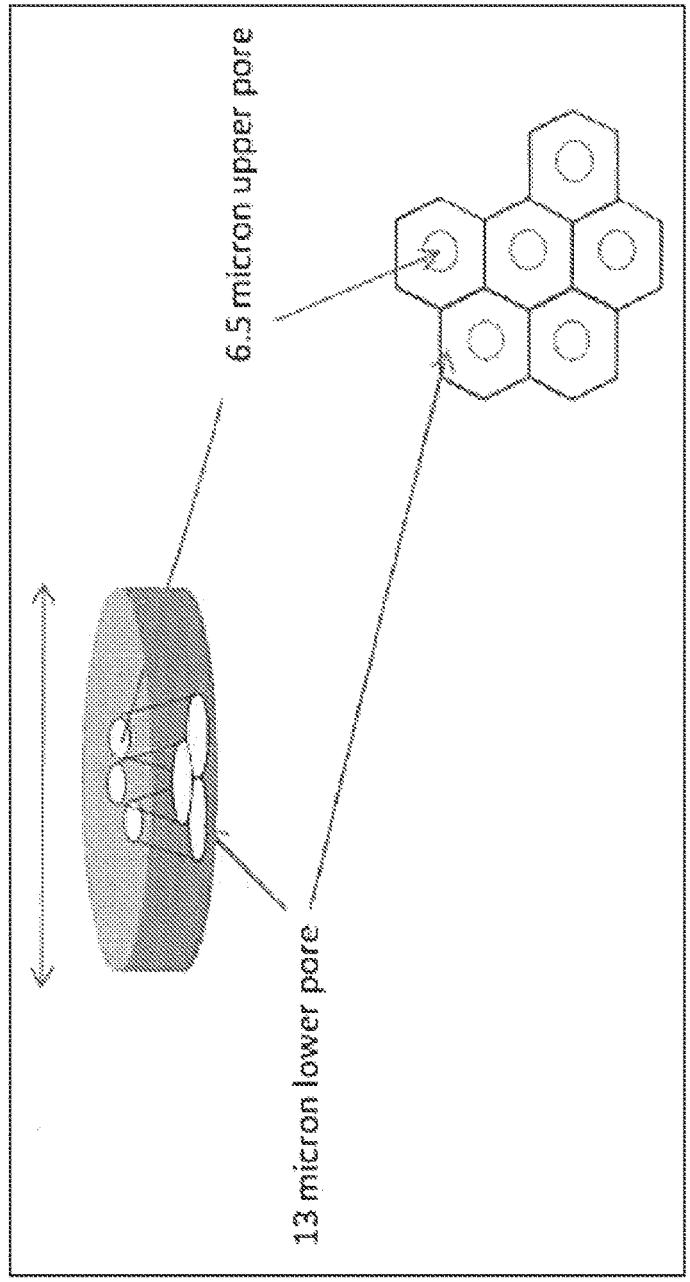
FIG. 17 is a diagram illustrating a filter with a regular pattern of 6.5-μm-diameter conical pores, according to some embodiments.

In some embodiments, as shown in FIG. 16, the inside surfaces 1600 of one or more pores and/or the bottom surface 1602 of the filter (i.e., the portion designed to be in contact with the wick) are treated and/or coated with one or more super-hydrophilic substances (e.g., titanium dioxide, Hydak® hydrophilic coating (available from Biocoat Inc. (Horsham, Pa.), polyvinylpyrrolidone (PVP), and/or chitosan) to improve the initiation of capillary wicking between the filter and the wick. In some embodiments, the bottom surface of the filter is treated and/or coated with one or more substances that promote the mobilization of specific cells to move through the filter. For example, a chemotactic substance may be added such that contaminating large myeloid cells leave the top surface of the filter and are removed as waste.

In some embodiments, the top surface of the filter (i.e., the portion designed to retain target cells) may be treated and/or coated with one or more substances (e.g., collagen and/or fibronectin) to improve attachment of target cells to the filter and/or growth of target cells on the filter. In other embodiments, the top surface of the filter may be modified to prevent attachment and/or growth of cells. In some embodiments, the top surface of the filter may be treated and/or coated with a hydrophobic outer ring such that fluid sitting on the top surface of the filter remains on the hydrophilic inner surface of the filter and does not overflow.

The number of pores and pore size used in any particular application will depend on the relative size of the target cells and non-target cells. In some embodiments, as shown in FIGS. 17 and 18A-18E, the pores are distributed in a pattern. A suitable filter may include between about 50,000 pores/$cm^2$ and about 200,000 pores/$cm^2$ (e.g., 75,000 pores/$cm^2$ to 150,000 pores/$cm^2$; 90,000 pores/$cm^2$ to 115,000 pores/$cm^2$; or 95,000 pores/$cm^2$ to 110,000 pores/$cm^2$). In some embodiments, a filter has approximately 100,000 pores/$cm^2$.

Naturally, at least most of the non-target cells in a fluid sample containing cells will have diameters (or largest dimensions) significantly smaller than that of the target cells in the fluid sample and smaller than the diameter (or largest dimension) of the pores in a filter of interest.

According to some embodiments, a filter includes a plurality of cylindrical- and/or conical-shaped pores. Target cells to be retained on a filter generally may have a diameter (or longest dimension) of more than about 20 µm and less than about 50 µm. The length of each pore may range from about 10 µm to about 50 µm. A conical pore comprises a narrow end and a wide end, and has a substantially circular diameter that directly or ultimately tapers from the wide end to the narrow end. Each conical pore may be oriented within the filter and system such that cells enter the narrow end of the pore and exit the wide end of pore. The narrow entrance end of a conical pore may range from about 5.5 µm to about 8.0 µm in diameter. In some embodiments, as shown in FIGS. 17 and 18A-18E, each pore has a narrow entrance end with an average diameter of approximately 6.5 µm and a wider exit end with an average diameter of approximately 13 µm. The pitch of each conical pore may vary, and the pitch of a single conical pore may change along the length of the pore. In some embodiments, a conical pore has a constant angle from about 1° to about 45°, such as about 13°. In FIGS. 17 and 18A-18E, each conical pore is constructed such that the surface facing the upper compartment or tank has a regular pattern of 6.5-µm-diameter openings, and the opening of each pore on the opposite face of the filter has a diameter of at least twice that distance, in accordance with some embodiments.

A filter may be mechanically and/or thermally stable. The filter may be optically transparent in visible and/or ultraviolet spectrum light (e.g., constructed from a glass and/or polymer). The filter may be biologically compatible for downstream genotype and/or phenotype analyses. In some embodiments, the filter is two-dimensional with high density and pores that cause the target cells to be retained on and/or in the filter. Each pore may communicate with opposite outer surfaces of the filter. The thickness of the filter may range from about 20 µm to about 200 µm, depending on the material used. In some embodiments, the filter is approximately 30 µm thick.

According to some embodiments, the filter is composed of one or more biocompatible materials including, for example, a biocompatible polymer. In some embodiments, one or more of the biocompatible materials are biodegradable. In other embodiments, one or more of the biocompatible materials are non-biodegradable. Representative biocompatible polymers include, but are not limited to, poly (ester amide), polyhydroxyalkanoates (PHA), poly(3-hydroxyalkanoates) such as poly(3-hydroxypropanoate), poly(3-hydroxybutyrate), poly(3-hydroxyvalerate), poly(3-hydroxyhexanoate), poly(3-hydroxyheptanoate) and poly(3-hydroxyoctanoate), poly(4-hydroxyalkanaote) such as poly(4-hydroxybutyrate), poly(4-hydroxyvalerate), poly(4-hydroxyhexanote), poly(4-hydroxyheptanoate), poly(4-hydroxyoctanoate) and copolymers including any of the 3-hydroxyalkanoate or 4-hydroxyalkanoate monomers described herein or blends thereof, poly(D,L-lactide), poly(L-lactide), polyglycolide, poly(D,L-lactide-co-glycolide), poly(L-lactide-co-glycolide), polycaprolactone, poly(lactide-co-caprolactone), poly(glycolide-co-caprolactone), poly(dioxanone), poly(ortho esters), poly(anhydrides), poly(tyrosine carbonates) and derivatives thereof, poly(tyrosine ester) and derivatives thereof, poly(imino carbonates), poly(glycolic acid-co-trimethylene carbonate), polyphosphoester, polyphosphoester urethane, poly(amino acids), polycyanoacrylates, poly(trimethylene carbonate), poly(iminocarbonate), polyurethanes, polyphosphazenes, silicones, polyesters, polyolefins, polyisobutylene and ethylene-alphaolefin copolymers, acrylic polymers and copolymers, vinyl halide polymers and copolymers, such as polyvinyl chloride, polyvinyl ethers, such as polyvinyl methyl ether, polyvinylidene halides, such as polyvinylidene chloride, polyacrylonitrile, polyvinyl ketones, polyvinyl aromatics, such as polystyrene, polyvinyl esters, such as polyvinyl acetate, copolymers of vinyl monomers with each other and olefins, such as ethylene-methyl methacrylate copolymers, acrylonitrile-styrene copolymers, ABS resins, and ethylene-vinyl acetate copolymers, polyamides, such as Nylon 66 and polycaprolactam, alkyd resins, polycarbonates, polyoxymethylenes, polyimides, polyethers, poly(glyceryl sebacate), poly(propylene fumarate), poly(n-butyl methacrylate), poly(sec-butyl methacrylate), poly(isobutyl methacrylate), poly(tert-butyl methacrylate), poly(n propyl methacrylate), poly(isopropyl methacrylate), poly(ethyl methacrylate), poly(methyl methacrylate), epoxy resins, polyurethanes, rayon, rayon-triacetate, cellulose acetate, cellulose butyrate, cellulose acetate butyrate, cellophane, cellulose nitrate, cellulose propionate, cellulose ethers, carboxymethyl cellulose, copoly(ether-esters) (e.g., poly(ethylene oxide/poly(lactic acid) (PEO/PLA))), polyalkylene oxides such as poly(ethylene oxide), poly(propylene oxide), poly(ether ester), polyalkylene oxalates, polyphosphazenes, phosphoryl choline, choline, poly(aspirin), polymers and co-polymers of hydroxyl bearing monomers such as 2-hydroxyethyl methacrylate (HEMA), hydroxypropyl methacrylate (HPMA), or hydroxypropylmethacrylamide, carboxylic acid bearing monomers such as methacrylic acid (MA), acrylic acid (AA), alkoxymethacrylate, alkoxyacrylate, and 3-trimethylsilylpropyl methacrylate (TMSPMA). In some embodiments, the filter includes ultraviolet-curable polyethylene glycol diacrylate (PEGDA), which can be easily functionalized to tune the protein and/or cell adhesion properties of the filter surface(s). See also, for example, U.S. Pat. No. 7,887,572, granted Feb. 15, 2011, corresponding to U.S. patent application Ser. No. 12/509,222, filed Jul. 24, 2009, which is hereby incorporated by reference in its entirety.

A filter may be produced by standard fabrication procedures including, but not limited to, micro-aspiration-assisted molding. The filter also may be a track-etched filter or membrane, such as a polycarbonate track-etched filter. Polycarbonate track-etched filters may be manufactured with a range of pore sizes, diameters, and pore densities by, for example, GE Healthcare Life Sciences (Piscataway, N.J.), EMD Millipore (Billerica, Mass.), Membrane Solutions, LLC (Plano, Tex.), or it4ip (Seneffe, Belgium).

For some embodiments, one or both surfaces of a filter are modified by, for example, immobilization of one or more compounds and/or other treatment to render the surface more or less hydrophilic. For example, one or more of a growth factor, an extracellular matrix protein, an enzyme, a reporter molecule, a liposome, and/or a nucleic acid may be immobilized on a surface of the filter. Non-limiting examples of growth factors include epidermal growth factor (EGF), platelet derived growth factor (PDGF), keratinocyte growth factor (KGF), a fibroblast growth factor (FGF), and a transforming growth factor (TGF). Non-limiting examples of extracellular matrix proteins include collagen, laminin, fibronectin, and heparan sulfate.

In some embodiments, one or more reporter molecules are immobilized on a filter such that cell growth can be detected during culture of the cells captured by the filter or after implantation of the filter in an immunodeficient non-human animal. For example, when the target cell is a tumor cell, a reporter molecule may include a fluorophore-quencher dual-labeled probe that is a substrate for a metalloproteinase (MMP). For example, a substrate such as MCA-Pro-Leu-Gly-Leu-DPA-Ala-Arg-NH, where MCA refers to methoxycoumarin and DPA refers to dinitrophenyl, may be used. Most MMPs associated with tumor growth can cleave such as substrate. Fluorescent MCA is quenched by DPA until the peptide is cleaved by a MMP between the Gly and Leu residues. Detecting of fluorescent MCA is indicative of growth of the cells. One of skill in the art will appreciate that other combinations of fluorophore and quencher molecules may be used.

In some embodiments, an in vivo targeted, activatable optical imaging probe based on a fluorophore-quencher pair bound to a targeting ligand is immobilized on a filter. See, for example, Ogawa et al., *Mol. Pharm.* 6(2):386-395 (2009), which is incorporated herein by reference in its entirety. With this system, fluorescence may be quenched by the fluorophore-quencher interaction outside target cells, but activated within target cells by dissociation of the fluorophore-quencher pair in lysosomes/endosomes. The rhodamine core fluorophore TAMRA and QSY7 quencher pair are particularly useful for in vivo imaging. Suitable target ligands include for example, a receptor ligand such as avidin, which is a non-covalently bound homotetrameric glycoprotein that binds to D-galactose receptor. D-galactose receptor is expressed on many cancer cells including ovarian, colon, gastric, and pancreatic cancer cells. A targeting ligand also can be an antibody or antigen-binding fragment thereof that has binding affinity for a tumor specific antigen such as human epidermal growth factor receptor type 2 (HER2) expressed on the cell surface of some tumors.

In some embodiments, an antibody or antigen-binding fragment thereof is immobilized on a filter. Such an antibody or antigen-binding fragment thereof may be immobilized on the filter before or after filtering the sample. It will be appreciated that immobilization of the antibody or fragment thereof on the filter, however, would not substantially contribute to the selection of target cells during the filtering process. Such an antibody or fragment thereof, however, may be useful for acting as a growth promoting ligand during the culture of the cells or after implantation in an immunodeficient non-human animal.

"Antibody" as the term is used herein refers to a protein that generally comprises heavy chain polypeptides and light chain polypeptides. Antigen recognition and binding occurs within the variable regions of the heavy and light chains. Single domain antibodies having one heavy chain and one light chain and heavy chain antibodies devoid of light chains are also known. A given antibody comprises one of five types of heavy chains, called alpha, delta, epsilon, gamma and mu, the categorization of which is based on the amino acid sequence of the heavy chain constant region. These different types of heavy chains give rise to five classes of antibodies, IgA (including IgA1 and IgA2), IgD, IgE, IgG (IgG1, IgG2, IgG3 and IgG4) and IgM, respectively. A given antibody also comprises one of two types of light chains, called kappa or lambda, the categorization of which is based on the amino acid sequence of the light chain constant domains. IgG, IgD, and IgE antibodies generally contain two identical heavy chains and two identical light chains and two antigen combining domains, each composed of a heavy chain variable region (VH) and a light chain variable region (VL). Generally IgA antibodies are composed of two monomers, each monomer composed of two heavy chains and two light chains (as for IgG, IgD, and IgE antibodies); in this way the IgA molecule has four antigen binding domains, each again composed of a VH and a VL. Certain IgA antibodies are monomeric in that they are composed of two heavy chains and two light chains. Secreted IgM antibodies are generally composed of five monomers, each monomer composed of two heavy chains and two light chains (as for IgG and IgE antibodies); in this way the IgM molecule has ten antigen binding domains, each again composed of a VH and a VL. A cell surface form of IgM also exists and this has two heavy chain/two light chain structure similar to IgG, IgD, and IgE antibodies.

"Antigen binding fragment" of an antibody as the term is used herein refers to an antigen binding molecule that is not a complete antibody as defined above, but that still retains at least one antigen binding site. Antibody fragments often include a cleaved portion of a whole antibody, although the term is not limited to such cleaved fragments. Antigen binding fragments can include, for example, a Fab, F(ab')2, Fv, and single chain Fv (scFv) fragment. An scFv fragment is a single polypeptide chain that includes both the heavy and light chain variable regions of the antibody from which the scFv is derived.

Other suitable antibodies or antigen binding fragments include, but are not limited to, linear antibodies, multispecific antibody fragments such as bispecific, trispecific, and multispecific antibodies (e.g., diabodies (see, e.g., Poljak, *Structure* 2(12):1121-23 (1994); Hudson et al., *J Immunol. Methods* 23(1-2):177-89 (1994)), triabodies, and tetrabodies); minibodies; chelating recombinant antibodies; intrabodies (Huston et al., *Hum. Antibodies* 10(3-4):127-42 (2001); Wheeler et al., *Mol. Ther.* 8(3):355-66 (2003); Stocks, *Drug Discov. Today* 9(22): 960-66 (2004)); nanobodies; small modular immunopharmaceuticals (SMIP); binding-domain immunoglobulin fusion proteins; camelid antibodies; camelized antibodies; and VHH containing antibodies.

Non-limiting examples of antibodies or antigen-binding fragments thereof that act as growth promoting ligands include anti-CD3 antibodies for T cell tumors; anti-Ig antibodies for B cell tumors; or antibodies that can induce dimerization of class 1 growth factor receptors. See, for example, Fuh, et al., *Science* 256:1677-80 (1992); Rui, et al., *Endocrinology* 135:1299-1306 (1994); Schneider, et al., *Blood* 89:473-82 (1997); Mahanta, et al., *PLOS ONE* 3(4): e2054 (2008); and Spaargaren, et al., *J Biol Chem.* 266(3): 1733-39 (1991).

Implantation in an Immunodeficient Non-Human Animal

After recovering one or more target cells on and/or in a filter, the filter may be implanted in a non-human animal according to some embodiments. The non-human animal may be an immunodeficient non-human animal (e.g., an immunodeficient rodent such as an immunodeficient mouse or rat). The immunodeficient non-human animal may be homozygous for the severe combined immune deficiency (SCID) spontaneous mutation (Prkdcscid); homozygous for the nude spontaneous mutation (Foxn1nu/nu); homozygous for a Rag1 mutation; homozygous for a Rag2 mutation; and/or homozygous for both the Rag1 and the Rag2 mutations. Suitable immunodeficient non-human animals (e.g., immunodeficient mice) are commercially available from, for example, The Jackson Laboratory (Bar Harbor, Me.).

In some embodiments, a filter is surgically implanted into the immunodeficient animal subcutaneously. For example, a filter may be implanted under the neural crest, under the adrenal gland capsule, in the peritoneal cavity, or in the flank of the animal. In some embodiments, a compound such as a growth factor and/or a reconstituted basement membrane matrix may be administered to the animal before, during, and/or after the filter is implanted.

In some embodiments, multiple filters are implanted in the same non-human animal, where each filter comprises one or more target cells. For example, one, two, three, or four filters may be implanted in the non-human animal. The filters may be implanted in different regions of the animal, for example, in each flank or in one flank and the abdomen of the animal. Each filter may be obtained from a single filtration device or may be obtained from separate filtration devices. However, when multiple filters are implanted into one animal, all of the filters should comprise cells recovered from the same patient.

In some embodiments, before implantation, a surface of the filter may be contacted with a composition that can transition from a liquid to gel phase without lethal or toxic effects on the target cells, for example, without the use of chemicals or temperatures that would harm living cells (i.e., kill and/or inhibit the proliferative capacity of the cells). For example, the composition may be a hydrogel composed of crosslinked polymer chains, natural or synthetic in origin, such as Puramatrix™ (a synthetic peptide matrix) available from 3DM, Inc. (Cambridge, Mass.) or a polyethylene (glycol) diacrylate-based, hyaluron-based, or collagen-based hydrogel available from Glycosan BioSystems (Salt Lake City, Utah). Such hydrogels may be applied in liquid form to a filter and then transitioned to gel phase by adding culture medium. A filter also may be contacted with a reconstituted basement membrane matrix like BD Matrigel™ Basement Membrane Matrix (available from BD Biosciences (San Jose, Calif.)) or a composition containing BD Matrigel™ and a culture medium. The composition also may include one or more extracellular matrix components, such as proteoglycans (e.g., heparan sulfate, chondroitin sulfate, and keratan sulfate), hyaluronic acid, collagen type IV, elastin, fibronectin, and laminin. Growth factors or other molecules may be added to the composition as needed for culture of the target cells.

In embodiments in which two or more filters are implanted, the filters may be stacked substantially on top of each other to produce a multi-layered three-dimensional culture device. Before stacking the filters, the surface of the filters may be contacted with a composition that can transition from a liquid to gel phase without lethal or toxic effects on the target cells (as described above). For example, the surface of the filter may be contacted with a reconstituted basement membrane matrix.

In some embodiments, before implantation, one or more filters may be cultured in a cell culturing device, for example, in the presence of a culture medium to, for example, assess target cell viability or increase target cell population. In some embodiments, once the number of target cells has increased, the target cells are removed from the filter (e.g., by washing) and implanted in the immunodeficient animal.

After implanting one or more filters in an immunodeficient non-human animal, the animal may be monitored for growth of the cells or development of a tumor. For example, to monitor cell growth, an implanted filter may include a substrate for a MMP or an in vivo activatable optical imaging probe (as discussed above). Development of a tumor in the animal may confirm the presence of tumor cells in the fluid sample and is indicative of the metastasis potential of the cells. If a tumor develops, it may be removed from the animal and subjected to further in vitro or in vivo characterization. For example, a tumor or cells isolated from the tumor may be subjected to genomic, proteomic, immunocytochemical, or other molecular assays to further characterize the tumor and/or cells thereof. In some embodiments, tissue specific and/or tumor specific reagents such as antibodies, probes, or PCR primers may be used to examine a tumor and/or cells thereof.

In embodiments in which the growth of tumor cells has been confirmed in the animal model, the responsiveness of the cells to one or more chemotherapeutic agents may be assessed by administering a chemotherapeutic of interest to the animal and monitoring responsiveness (e.g., by monitoring cell growth or cell death).

The invention is further described in the following examples, which do not limit the scope of the invention described in the claims.

Example 1—Methods of Using a Filtration Device

This non-limiting example illustrates a general method of using a filtration device according to some embodiments. The filtration device is about 19 cm long and includes a circular track-etched polycarbonate filter with a smooth, flat, and hydrophilic surface. The filter includes a plurality of circular pores, each having a diameter of about 6.5 µm, randomly distributed throughout the filter (about $1 \times 10^5$ pores/cm$^2$).

FIG. 19 illustrates a method of using a filtration device according to some embodiments. As shown in step 1900 of FIG. 19, the cap of the compartment or tank of the filtration device is removed so that a sample (e.g., diluted blood or another source of cells in a fluid) may be transferred into the filtration device. In step 1902, before transfer/filtration and in order to lyse RBCs, about 3-ml to about 6-ml blood samples (e.g., drawn in standard EDTA tubes) are diluted with about 3 ml to about 1 ml of buffer solution, respectively. That is, a 3-ml blood sample is diluted with about 3 ml of buffer solution while a 6-ml blood sample is diluted with about 1 ml of buffer solution. After mixing the sample and dilution buffer solution, the samples are incubated for about 2 minutes at room temperature. Then, about 2.6 ml to about 1.6 ml of culture medium are added to the samples, respectively, for a total sample volume of about 8.6 ml each.

In step 1904, the sample is introduced into the compartment or tank of the filtration device. In steps 1906 and 1908, the sample begins to pass through the filter, being capillarized by a hyper-hydrophilic wick underneath and in close contact with the filter. Filtration of such sample volumes is usually complete within approximately 2 to 3 minutes (as verified by looking inside the tank).

Figure 20B:
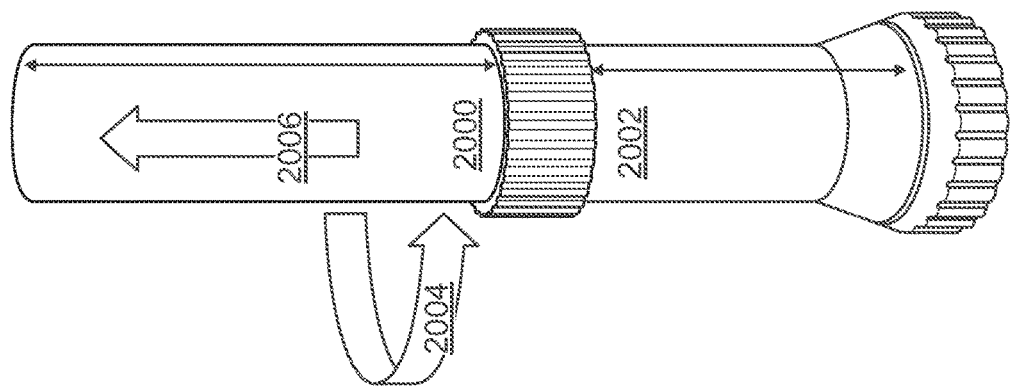
FIGS. 20A-20B show how to dissemble a filtration device according to some embodiments.
Figure 20A:
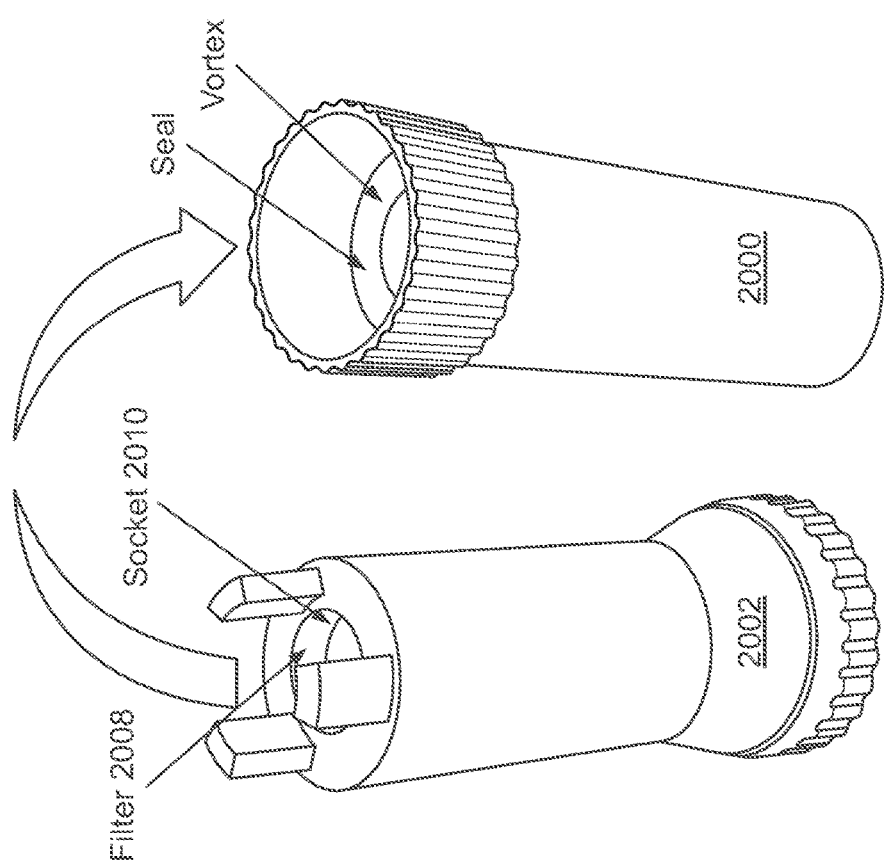

In steps 1910 and 1912, the upper part of the device is uncoupled or unclipped and detached from the lower part containing the wick and/or vacuum tube. This can be seen in detail in FIGS. 20A and 20B, which show a filtration device according to some embodiments. In FIG. 20A, the top part of the device (i.e., the compartment or tank) 2000 is uncoupled (e.g., unclipped) from the protective cylinder 2002 housing the hyper-hydrophilic wick so that the filter 2004 may be inserted or removed from the socket 2006. To introduce filter 2004, the lower cap of protective cylinder 2002 may be unscrewed about half way in the direction of arrow 2008 to make the wick inside somewhat loose. Then, filter 2004 is placed (e.g., bright side upward) in the socket 2006 above and in tight contact with the wick in the protective cylinder 2002. According to arrow 2010, the top part of the device 2000 is aligned (e.g., according to the letters) and coupled with the protective cylinder 2002. In FIG. 20B, the top part of the device 2000 is recoupled to the protective cylinder 2002. By pushing the top part of the device 2000 downward in the direction of arrow 2012, the filter 2004 is secured in the socket 2006. The top part of the device 2000 may be further recoupled/clipped by turning or twisting the top part of the device 2000 onto the protective cylinder 2002 in the direction of arrow 2014. To remove filter 2004, the top part of the device 2000 may be decoupled/unclipped by turning or twisting the top part of the device 2000 off of the protective cylinder 2002 in a direction opposite of arrow 2014 and pulling the top part of the device 2000 upward in the direction opposite of arrow 2012. After use, the upper part of the device 2000 may be cleaned for reuse, recycled, and/or discarded.

Returning FIG. 19, in step 1914, the filter, which may be inserted in an alcove or socket above the wick in the lower part of the device or held in the top part of the device, is removed (e.g., with a forceps or by evenly pushing down a rod located at the bottom of the filtration device) and blotted down on, for example, a piece of Whatman® paper (available from GE Healthcare Life Sciences (Piscataway, N.J.)) with the captured cells on the upper face of the filter. The filter may be transferred onto a glass slide or released into a well of a 24-well tissue culture plate. Adequate tissue culture medium and growth factors may be added to the slide or well. The filtration area of the device filter is delimited by an O-shaped ring (i.e., a filter support) made of surgical inox and marked with a unique numeric code to insure traceability of each filtered sample.

In order to increase the number of (rare) target cells obtained from a sample, target cells may be recovered from multiple portions of the same diluted blood sample. Each portion may be filtered through a different filtration device. When multiple filters are obtained, the filters may be laid successively upon each other (as described above). For example, a filter may be released from a filtration device and placed on a 100-µl layer of 1:1 BD Matrigel™/Medium (M/M). A 70-μl layer of M/M is added to the top of the filter and each successive filter before laying down the next filter. At the end of the process, the last filter is covered with a 70-μl layer of M/M, and a sufficient volume of culture medium (e.g., culture medium containing fetal calf serum (FCS)) is added to coat the stack of filters and provide a three-dimensional culture device. The three-dimensional device may be used to transport and/or culture the cells, and also may be implanted in an immunodeficient animal.

Figures 21A, 21B:
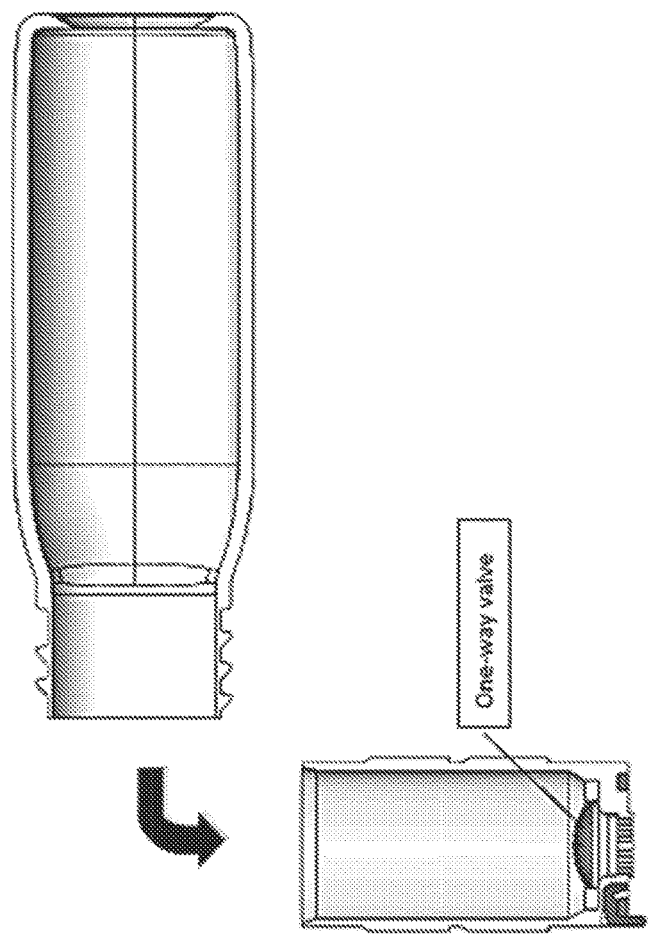
FIGS. 21A-21F illustrate a method of using the filtration device from FIGS. 10A-10C, 11A-11B, and 12, according to some embodiments.
Figures 21C, 21D, 21E:
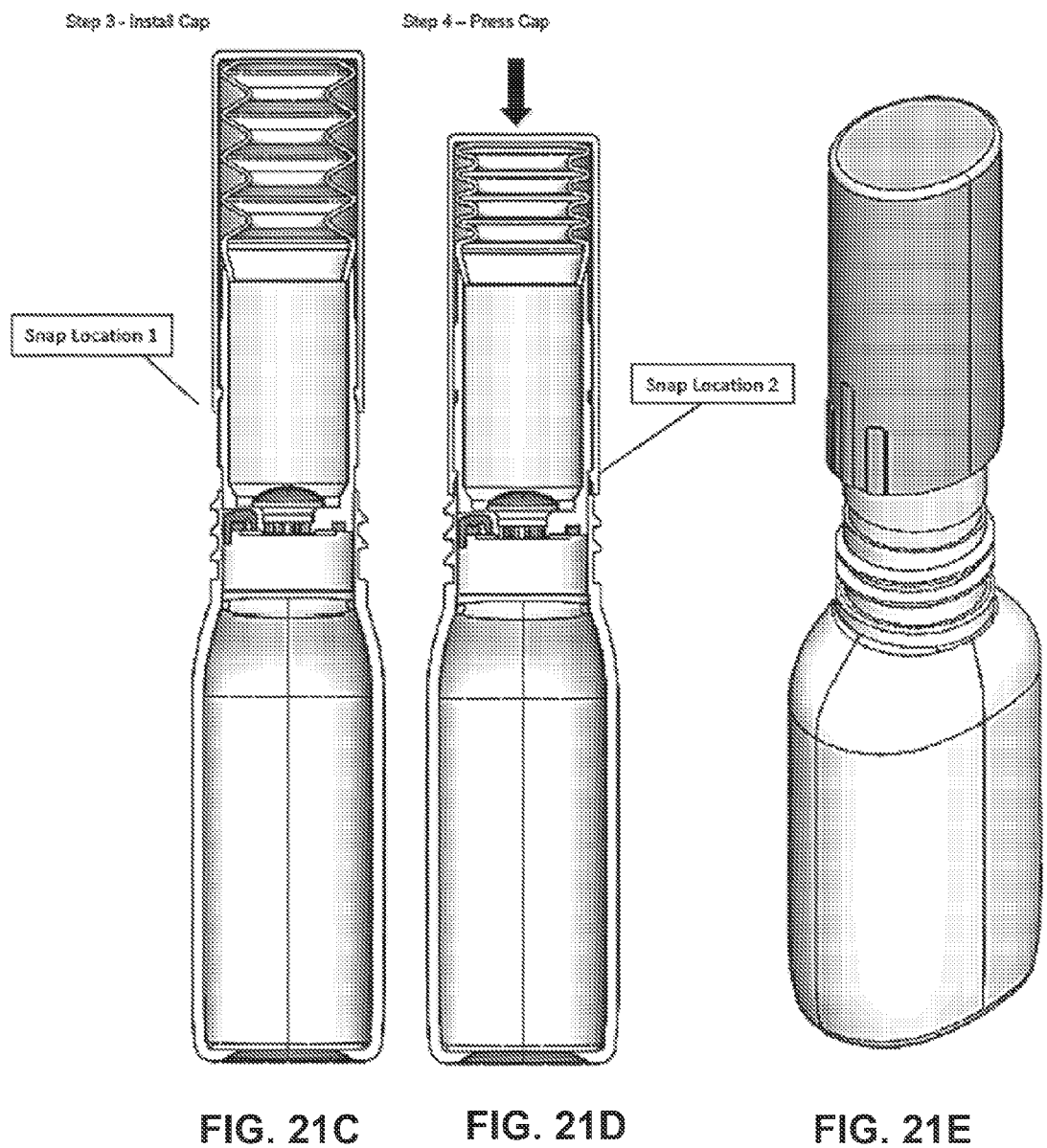
Figure 21F:
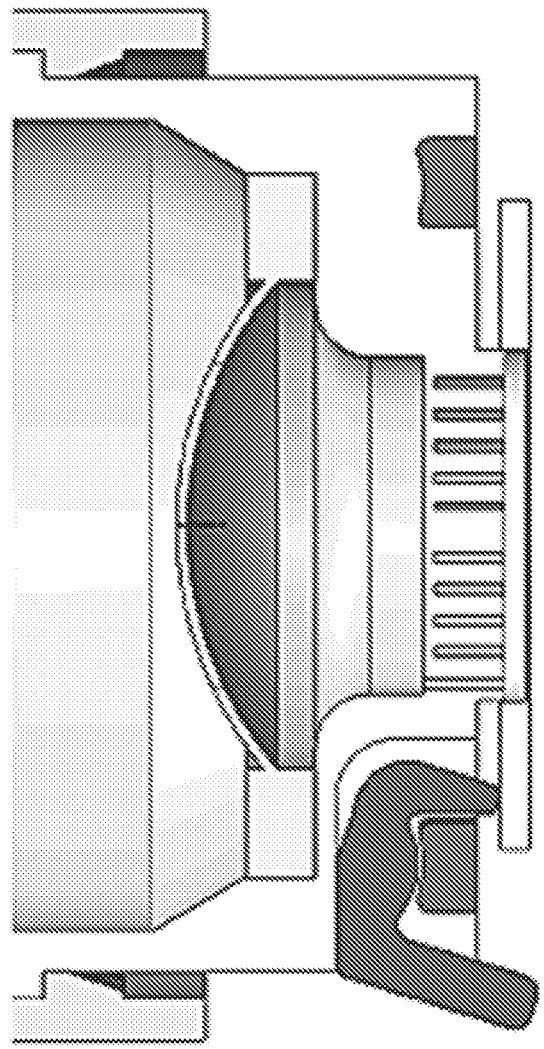

FIGS. 21A-21F illustrate a method of using the filtration device from FIGS. 10A-10C, 11A-11B, and 12, according to some embodiments. First, in FIG. 21A, the cap of the filtration device is removed. Next, in FIG. 21B, the buffer solution and blood sample are poured from a container into the receiving compartment of the filtration device, which has a one-way valve at its bottom. Then, in FIG. 21C, the container is repurposed as a waste container by being removable fastened (e.g., snap-locked) to the bottom of the filtration device. The cap is replaced and also removably fastened (e.g., snap-locked) to the top of the filtration device. Formed inside the cap is a member having evenly spaced, parallel folds like the bellows of an accordion. In FIG. 21D, a user presses the cap downward, which compresses the folds of the accordion-like member. After filtration in FIG. 21E, the filter may be ejected from the filtration device as shown in FIG. 21F, and the waste container may be discarded.

Example 2—Sensitivity for Detecting CTCs

The sensitivity of a filtration device for isolating CTCs was assessed, according to some embodiments, as follows. Twenty-five independent experiments were conducted with fixed H2030 cells (an adenocarcinoma non-small cell lung cancer cell line available as Catalog No. CRL-5914™ from the American Type Culture Collection (ATCC) (Manassas, Va.)). The H2030 cells were cultured in flasks containing RPMI 1640 supplemented with 10% FCS and harvested by trypsinization. Cell viability was assessed by trypan blue exclusion. The cells were used in the experiments described below if viability was estimated to exceed 90%.

After fixation with formaldehyde, the H2030 cells were spiked into whole peripheral blood drawn from a healthy donor to yield a final concentration of 2 or 5 fixed H2030 cells per 1 mL of blood, and filtered through a filtration device according to some embodiments, as set forth in Example 1. The average filtration time was 50 seconds. Cells on the filters were stained with hematoxylin and eosin, and counted. The number of H2030 cells spiked into the blood sample versus the actual number of H2030 cells recovered in the sample is shown in TABLES 1 and 2. For the samples spiked with 5 cells, the average percentage of H2030 cells recovered was 91.2%, with an average of 4.56±0.71 cells recovered, and no fewer than 3 cells detected in all 25 samples (see TABLE 1).

TABLE 1

|  | | Exp. #1 | Exp. #2 | Exp. #3 | Exp. #4 | Exp. #5 | Total |
|---|---|---|---|---|---|---|---|
| Number of Cells Spiked in 1 mL of Blood per Filter | | 5 | 5 | 5 | 5 | 5 | 25 |
| Number, | Filter#1 | 4, 80 | 5, 100 | 4, 80 | 5, 100 | 4, 80 | 22 |
| Percentage | Filter#2 | 5, 100 | 5, 100 | 5, 100 | 3, 60 | 5, 100 | 23 |
| of Cells | Filter#3 | 3, 60 | 4, 80 | 5, 100 | 5, 100 | 5, 100 | 22 |
| Recovered | Filter#4 | 5, 100 | 4, 80 | 4, 80 | 5, 100 | 5, 100 | 23 |
| per Filter | Filter#5 | 4, 80 | 5, 100 | 5, 100 | 5, 100 | 5, 100 | 24 |
| Total Number of Spiked Cells | | 25 | 23 | 25 | 25 | 25 | 125 |
| Total Number of Isolated Cells | | 21 | 23 | 23 | 23 | 24 | 114 |
| Average Percentage Recovery per Filter | | 84 | 92 | 92 | 92 | 96 | 91.2 |

For the samples spiked with 2 cells, the average percentage of H2030 cells recovered was 74%, with an average of 1.480±0.71 cells recovered (see TABLE 2).

TABLE 2

|  | | Exp. #1 | Exp. #2 | Exp. #3 | Exp. #4 | Exp. #5 | Total |
|---|---|---|---|---|---|---|---|
| Number of Cells Spiked in 1 mL of Blood per Filter | | 2 | 2 | 2 | 2 | 2 | 10 |
| Number, | Filter#1 | 2, 100 | 1, 50 | 2, 100 | 1, 50 | 2, 100 | 8 |
| Percentage | Filter#2 | 2, 100 | 1, 50 | 0, 0 | 2, 100 | 2, 100 | 7 |
| of Cells | Filter#3 | 0, 0 | 2, 100 | 2, 100 | 1, 50 | 2, 100 | 7 |
| Recovered | Filter#4 | 2, 100 | 2, 100 | 1, 50 | 0, 0 | 2, 100 | 7 |
| per Filter | Filter#5 | 2, 100 | 1, 50 | 2, 100 | 1, 50 | 2, 100 | 8 |
| Total Number of Spiked Cells | | 10 | 10 | 10 | 10 | 10 | 50 |
| Total Number of Isolated Cells | | 8 | 7 | 7 | 5 | 10 | 37 |
| Average Percentage Recovery per Filter | | 80 | 70 | 70 | 50 | 100 | 74 |

To verify whether the percentage of cell loss was related to the filtration device, H2030 cells were harvested as indicated above, fixed, and pipetted directly into an Eppendorf tube containing filtration buffer solution. Cells were recovered using a Cytospin™ centrifuge (available from Thermo Fisher Scientific (Waltham, Mass.) and stained with hematoxylin and eosin. Under these conditions, the mean percentage of recovery was 82% for samples spiked with 2 cells and 88% for samples spiked with 5 cells. For the samples spiked with 2 cells, an average of 1.64±0.57 cells was recovered. For the samples spiked with 5 cells, an average of 4.40±0.71 cells was recovered. The relative sensitivities of the filtration device versus direct cell collection were assessed through P-values calculated for unpaired unilateral Student test (0.19 and 0. for 2 and 5 spiked cells, respectively), unpaired bilateral Student test (0.39 and 0.41 for 2 and 5 cells respectively), and Fisher test (0.14 and 0.34 for 2 and 5 cells respectively). These tests showed that collection of 2 or 5 spiked tumor cells through the filtration device or by direct collection of the micropipetted cells directly into an Eppendorf tube resulted in similar sensitivities. Through the different series of tests using the filtration device and direct collection, similar numbers of cells were lost after 25 independent collections of 2 or 5 spiked tumor cells. Indeed, the percentage of cells lost through the filtration device was 26% (standard deviation (SD) was 0.71 with 0.52 cells lost on average), and 9% (SD was 0.65 with 0.44 cells lost on average) for 2 and 5 spiked H2030 cells respectively, while it was 18% (SD was 0.57 with 0.36 cells lost on average) and 12% (SD was 0.71 with 0.60 cells lost on average) through direct collection. The P-value for unpaired unilateral Student test indicated similar numbers of lost cells using the filtration device or by direct collection with 2 or 5 tumor cells.

No significant differences were found when using the P-value for the unpaired unilateral Student test to compare the results obtained with 2 versus 5 spiked tumor cells through the filtration device or by direct collection (0.19 versus 0.20 for 2 and 5 spiked tumor cells, respectively). Furthermore, no significant differences were found when using the P-value for the unpaired unilateral Student test to compare the 25 results obtained with 2 versus 5 spiked tumor cells through the filtration device (0.34) or by direct collection (0.10). Altogether, these results indicate that cells were lost essentially through micropipetting and that the recovery rate of the filtration device was close to 100%.

Example 3—Viability and Culture of Target Cells

Five independent experiments were conducted to assess the viability of tumor cells after filtration through a filtration device according to some embodiments. H2030 cells were cultured in flasks containing RPMI 1640 supplemented with 10% FCS and harvested by trypsinization. Fifty live H2030 cells were filtrated through the filtration device as described in Example 1. Viable cells were counted immediately after filtration using the trypan blue exclusion test.

Figure 22B:
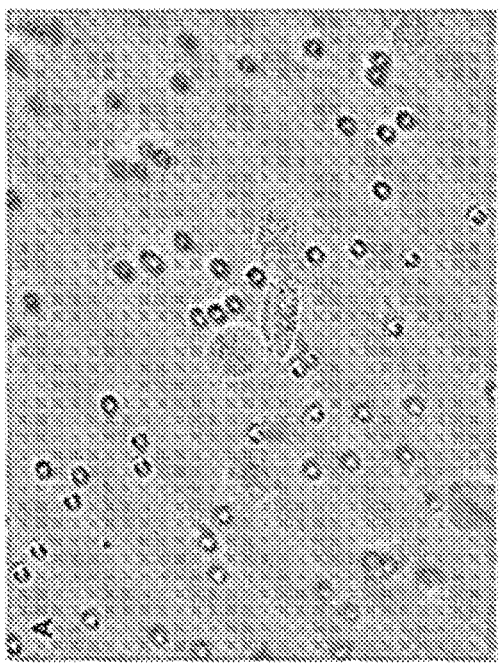
FIG. 22B is a photomicrograph of the cells from FIG. 22A, after 4 days in culture medium, according to some embodiments.
Figure 22A:
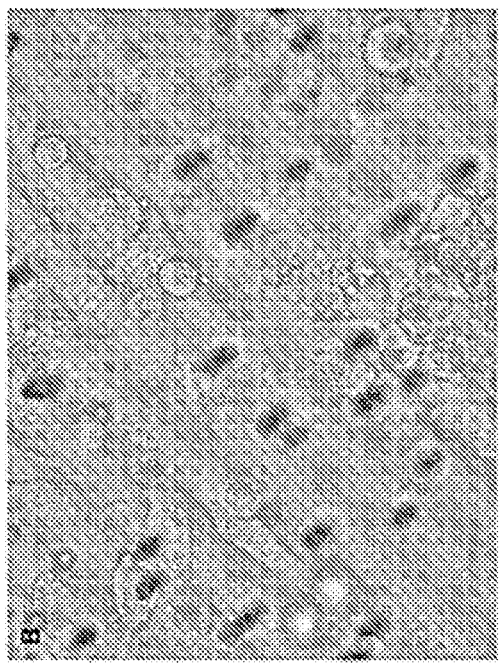
FIG. 22A is a photomicrograph of live H2030 cells following filtration through a filtration device, according to some embodiments.

FIG. 22A is a photomicrograph (×40) of live H2030 cells following filtration through a filtration device, according to some embodiments. The mean percent recovery was 85%±9%. The capacity of isolated H2030 cells to grow in tissue culture was further evaluated in eight independent experiments. In each experiment, isolated H2030 cells were able to grow and expand on the filter under adequate tissue culture conditions. FIG. 22B is a photomicrograph of the cells from FIG. 22A, after 4 days in culture medium, according to some embodiments.

Figure 23B:
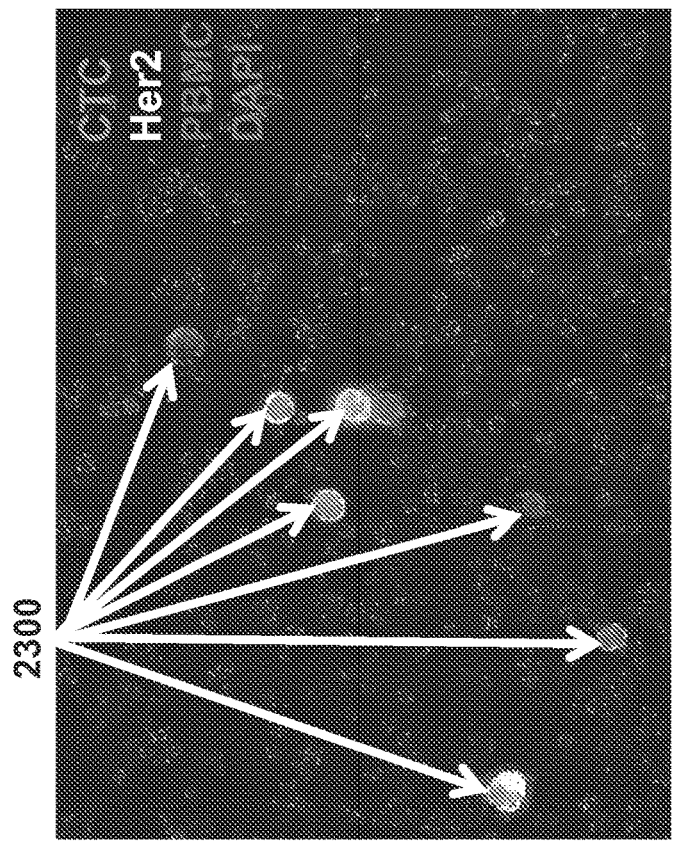
FIGS. 23A-23B show a fluorescence image of SKBR3 tumor cells that were spiked in donor blood and spread on a glass slide without filtering.
Figure 23A:
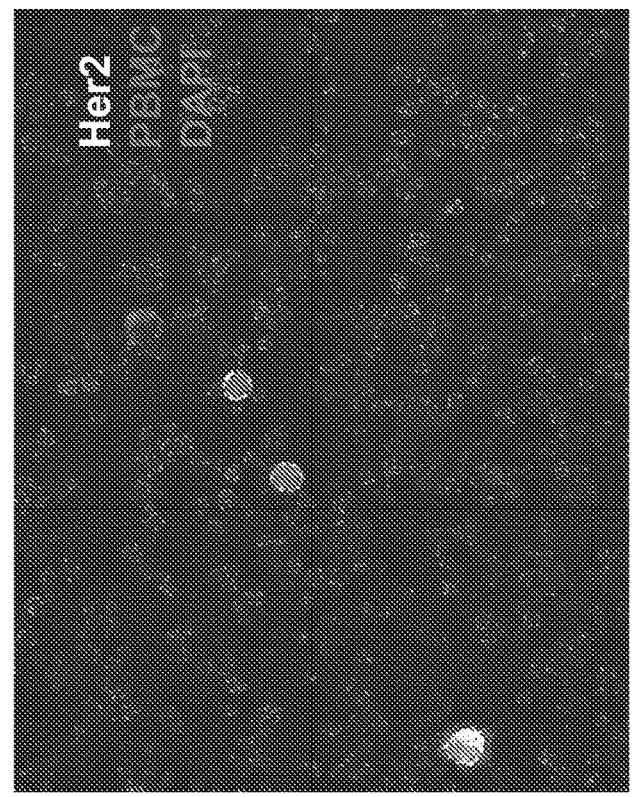

FIGS. 23A and 23B show a fluorescence image of SKBR3 breast cancer tumor cells that were spiked in normal human donor blood, which was spread on a glass slide and hybridized to specific RNA probes, without filtering. The RNA probes included a red probe for PBMCs that hybridizes to CD45, a green probe that hybridizes to epcam, an epithelial cell marker and a biomarker for tumor cells, and a white probe that hybridizes to HER2, also a biomarker for tumor cells. In FIG. 23A, a large number of cells and proteins are visible, including PBMCs, the biomarker HER2, and the fluorescent stain DAPI (4',6-diamidino-2-phenylindole), which binds strongly to A-T rich regions in DNA and thus stains the nuclei of all cells blue. In FIG. 23B, the tumor cells 2300 are indicated among the many other cells and proteins from the donor blood.

Figure 24B:
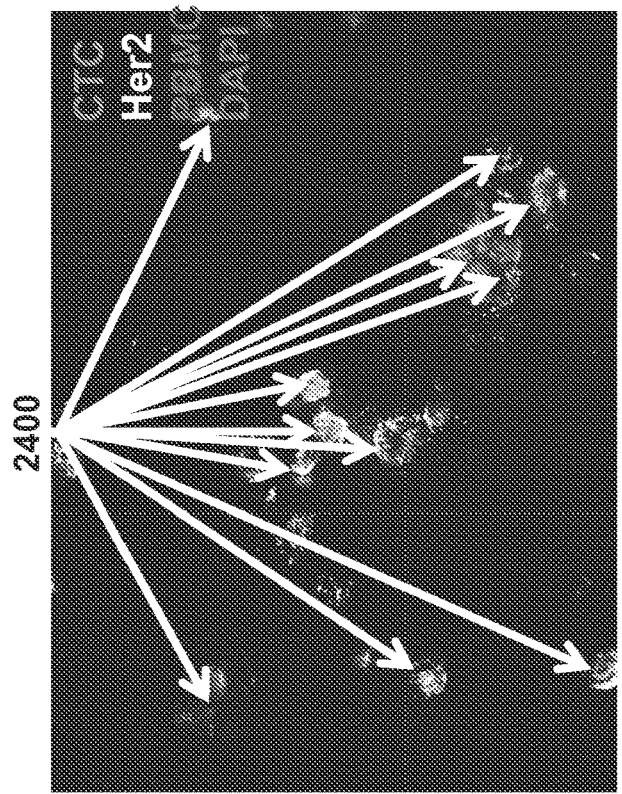
FIGS. 24A-24B and 25A-25B are fluorescence microscopy images of SKBR3 tumor cells that were spiked in donor blood and captured on a filter designed to eliminate PBMCs and RBCs, according to some embodiments of the present disclosure.
Figure 24A:
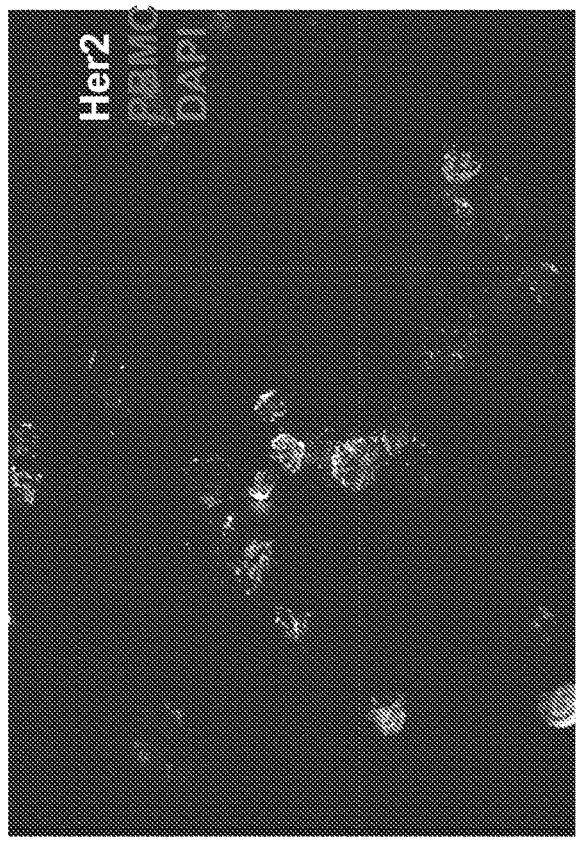
Figure 25B:
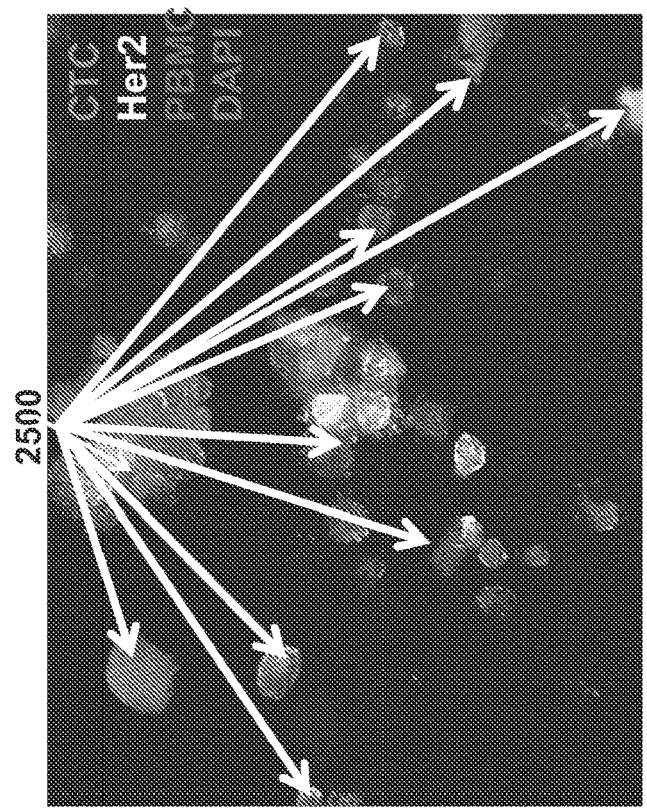
Figure 25A:
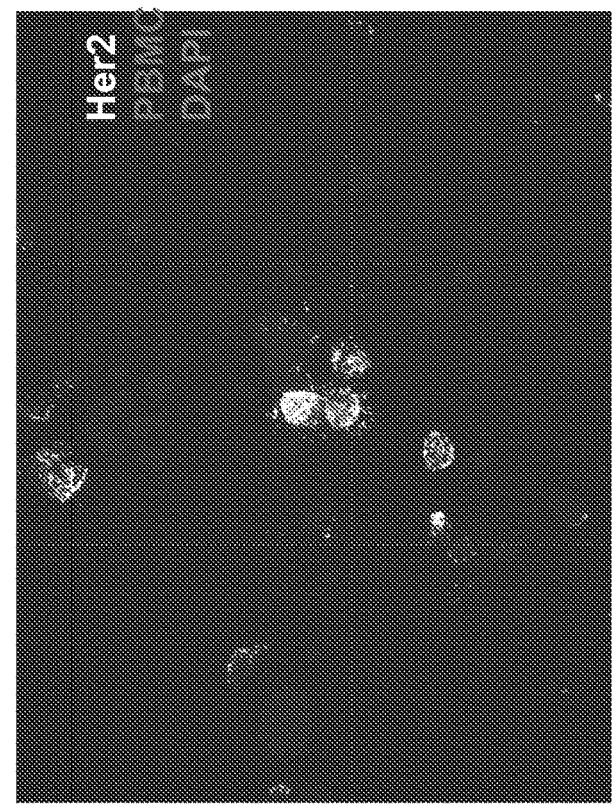

FIGS. 24A, 24B, 13A, and 13B show fluorescence images of SKBR3 breast cancer tumor cells that were spiked in normal human donor blood and captured on a filter designed to eliminate PBMCs and RBCs, according to some embodiments of the present disclosure. In FIG. 24A, fewer cells and proteins are visible in a first fluorescence image due to the filtering of PBMCs and RBCs; and in FIG. 24B, the tumor cells 2400 are indicated among the other remaining cells and proteins from the donor blood. Likewise, in FIG. 25A, fewer cells and proteins are visible in a second fluorescence image due to the filtering of PBMCs and RBCs; and in FIG. 25B, most of the remaining cells and proteins express epcam and HER2 and thereby appear to be tumor cells 2500.

Example 4—Recovery of Target Cells on a Filter

Figure 26:
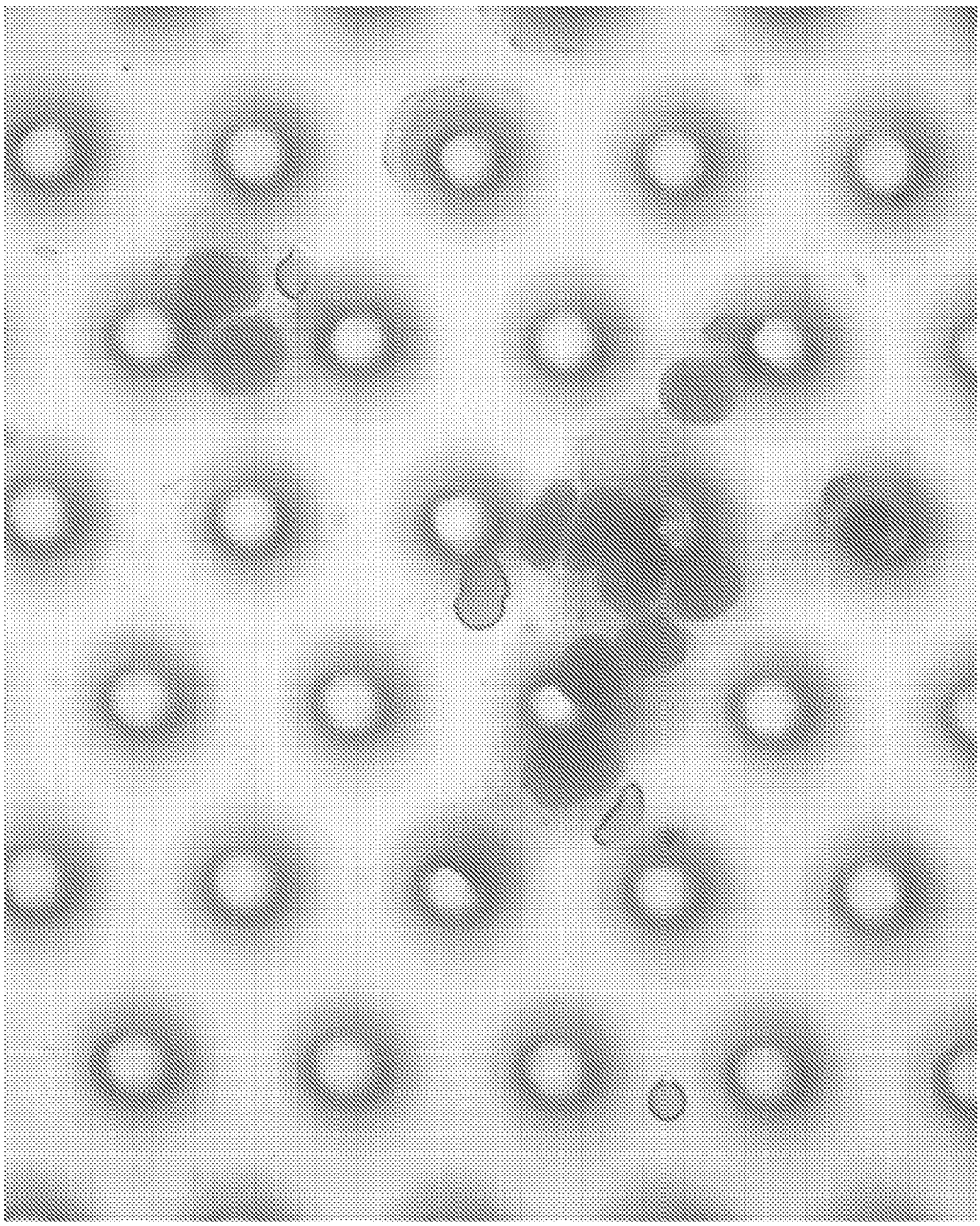
FIG. 26 is a fluorescence microscopy image of HT29 tumor cells that were spiked in donor blood and captured on a filter designed to eliminate PBMCs and RBCs, according to some embodiments of the present disclosure.

FIG. 26 is a fluorescence image of Giemsa-stained HT29 tumor cells spiked in normal blood and captured on a filter designed to eliminate PBMCs and RBCs, according to some embodiments of the present disclosure. A sample of 9 ml of human blood was collected in a K-EDTA tube, diluted with 12 ml of phosphate buffered saline (PBS), gently mixed, and loaded in the top tank of a filtration device according to some embodiments. Once the diluted sample passed through the filter, the filter was washed with two consecutive 1.0 ml washes with PBS. The wick was designed to handle the additional volume of liquid.

Following the washes, the top tank was removed to reveal the filter, which was removed and observed under a microscope. The filter was placed in a tissue culture plate to grow the captured cells, which were stained on the filter with standard histochemical stains, incubated for immunofluorescence (IF) or hybridized for fluorescence in situ hybridization for DNA(FISH) or in situ hybridization for RNA. According to some embodiments, the filter was flexible in order to be introduced into an Eppendorf tube to extract the cellular DNA and RNA.

Figure 27A:
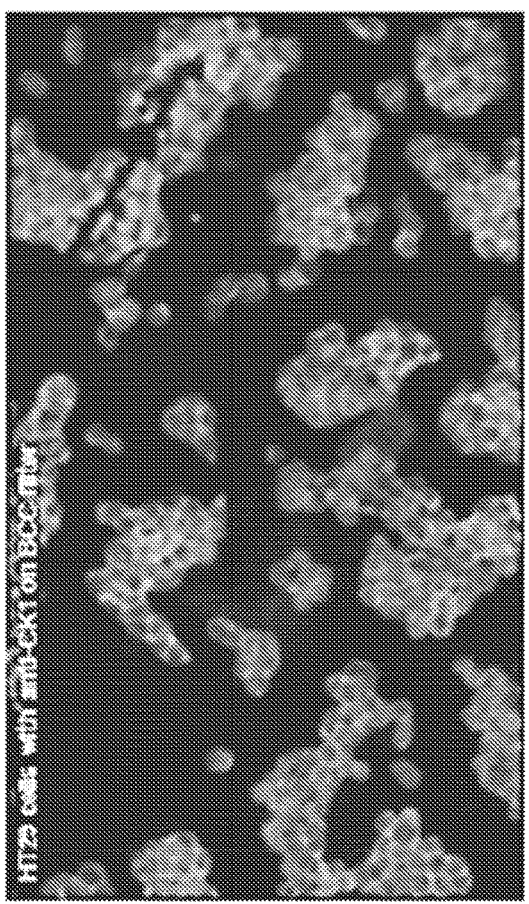
FIGS. 27A-27C are fluorescence microscopy images of HT29 tumor cells captured and grown on a filter coated with collagen, according to some embodiments of the present disclosure.
Figure 27B:
Figure 27C:
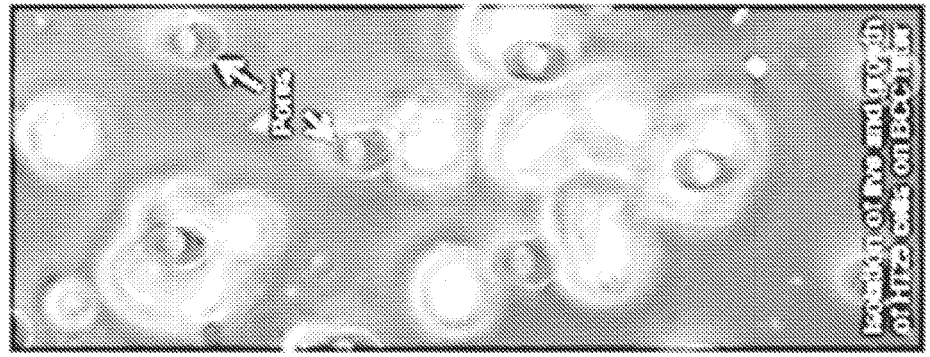

FIGS. 27A-27C are microscopy images of HT29 tumor cells captured and grown on a filter coated with collagen, according to some embodiments of the present disclosure.

As an example of alternative target cells, FIG. 28 is a series of fluorescence microscopy images of three fetal embryonic cells captured from a maternal blood sample, according to some embodiments of the present disclosure.

Example 5—Recovery of Target Cells on a Filter and Transfer of the Filter to an Immunodeficient Animal To demonstrate that CTCs can be transferred from a human patient to a mouse, human HT29 colorectal cancer cells were grown to 50% confluence and trypsinized to release the cells from the surface of the culture dish. The cells were washed in PBS and diluted to yield a final concentration of 10,000 cells per μl. Normal human blood was collected in a sterile blood collection tube (e.g., an EDTA Vacutainer®, available from BD Biosciences (San Jose, Calif.)) and used within 60 minutes of collection. Either 1000 or 10,000 HT29 cells were added to 6-ml samples of normal human blood, which was gently mixed. Each 6-ml blood sample containing the HT29 cells was diluted with 1 ml of a dilution buffer and incubated for 2 minutes at room temperature. After 2 minutes incubation, 1.6 ml of culture medium were added and the whole 8.6 ml of diluted blood then was passed through the filtration device described in Example 1. Upon completion of filtration, the filter was ejected onto a piece of sterile gauze. Sterile forceps were used to place the filter on a solidified pad containing 100 µl of a 1:1 ratio of Matrigel/Medium. This solidified M/M pad was used to keep cells hydrated during the surgical procedure.

The filter was implanted under the skin of a Rag2−/− immunodeficient mouse and cell growth was monitored by palpation. A tumor developed on both sides of the filter within 3 weeks. The mouse was sacrificed and the filter with attached tumor was removed and placed in a Petri dish. Cells from the tumor were cultured and stained with antibodies, confirming that the tumor was derived from HT29 cells. Thus, as shown in Herrmann, et al., PLOS ONE 5:1-10 (2010), which is incorporated herein by reference in its entirety, CD44high/CD24high/EpCAMhigh HT29 cells selected in vivo have a cancer stem cell phenotype.

CONCLUSION

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All publications, patent applications, patents, and other references mentioned herein are incorporated by reference in their entirety.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

It is to be understood that the disclosed subject matter is not limited in its application to the details of construction and to the arrangements of the components set forth in the following description or illustrated in the drawings. The disclosed subject matter is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods, and systems for carrying out the several purposes of the disclosed subject matter. It is important, therefore, that the claims be regarded as including such equivalent constructions insofar as they do not depart from the spirit and scope of the disclosed subject matter.

Although the disclosed subject matter has been described and illustrated in the foregoing exemplary embodiments, it is understood that the present disclosure has been made only by way of example, and that numerous changes in the details of implementation of the disclosed subject matter may be made without departing from the spirit and scope of the disclosed subject matter, which is limited only by the claims which follow.

The invention claimed is:

1. An apparatus for isolating one or more target cells from a fluid sample, the apparatus comprising:
a first chamber for receiving the fluid sample with a first opening at the top of the first chamber and a second opening at the bottom of the first chamber, the first opening configured to receive the fluid sample, the second opening configured to align with a removable filter, the removable filter having a first surface facing the interior of the first chamber and a second surface opposite the first surface, the removable filter defining a plurality of pores configured to retain the one or more target cells from the fluid sample on the first surface and/or in the plurality of pores and to pass any non-target cells and fluid from the fluid sample through the plurality of pores, each pore of the plurality of pores having a first diameter in the first surface, the first diameter being smaller than a diameter of the one or more target cells, and a second diameter in the second surface, the second diameter being greater than the first diameter;
a second chamber in communication with the first chamber through the plurality of pores for receiving the any non-target cells and the fluid from the fluid sample, the second chamber comprising a hydrophilic microporous wick structure configured to contact the removable filter and draw the any non-target cells and the fluid from the fluid sample by capillary forces such that the any non-target cells and the fluid from the fluid sample are drawn into the second chamber and the one or more target cells are isolated on the first surface of the removable filter.

2. The apparatus of claim 1, wherein the second chamber has a socket for receiving the removable filter.

3. The apparatus of claim 1, wherein the hydrophilic microporous wick structure is coated and/or treated with a super-hydrophilic substance.

4. The apparatus of claim 1, wherein the second surface of the removable filter is coated and/or treated with a super-hydrophilic substance.

5. The apparatus of claim 1, wherein an inner surface of at least one pore of the plurality of pores is coated and/or treated with a super-hydrophilic substance.

6. The apparatus of claim 3, wherein the super-hydrophilic substance is titanium dioxide.

7. The apparatus of claim 1, wherein the first surface of the removable filter is coated and/or treated with a substance that improves target cell attachment to and/or growth on the removable filter.

8. The apparatus of claim 7, wherein the substance that improves target cell attachment to and/or growth on the removable filter comprises at least one of collagen and fibronectin.

9. The apparatus of claim 1, wherein the first surface of the removable filter is coated and/or treated with a substance that prevents target cell attachment to the removable filter.

10. The apparatus of claim 1, wherein an outer ring of the first surface of the removable filter is coated and/or treated with a hydrophobic substance.

11. The apparatus of claim 1, wherein the second surface of the removable filter is coated and/or treated with a substance that promotes mobilization of specific types of cells to move through the plurality of pores.

12. The apparatus of claim 11, wherein the substance that promotes mobilization of specific types of cells to move through the plurality of pores comprises a chemotactic substance.

13. The apparatus of claim 1, wherein the removable filter comprises curable polyethylene glycol diacrylate (PEGDA).

14. The apparatus of claim 1, wherein the removable filter has a thickness between the first surface and the second surface of about 30 µm.

15. The apparatus of claim 1, wherein the first diameter of at least one pore of the plurality of pores is about 6.5 µm and the second diameter of the at least one pore of the plurality of pores is about 13.0 µm.

16. The apparatus of claim 1, wherein the first chamber is removably coupled to the second chamber.

17. The apparatus of claim 1, wherein an inner surface of the first chamber comprises at least one hydrophilic portion and at least one hydrophobic portion, the portions configured to create laminar flow of the fluid sample across the first surface of the removable filter.

18. The apparatus of claim 1, wherein the first chamber comprises a vortex generator with a plurality of semicircular blades angled to create laminar flow of the fluid sample across the first surface of the removable filter.

19. The apparatus of claim 17, wherein the amount of the laminar flow of the fluid sample across the first surface of the removable filter is calibrated to sweep cells off one or more dead areas on the first surface of the removable filter.

20. The apparatus of claim 1, wherein the fluid sample is at least one of a blood sample and a diluted blood sample.

21. The apparatus of claim 20, wherein the one or more target cells are at least one of tumor cells and fetal embryonic cells.

22. A method for isolating one or more target cells from a fluid sample, the method comprising:
introducing the fluid sample into a first chamber through a first opening at the top of the first chamber such that gravity cause the fluid sample to flow downward to a second opening at the bottom of the first chamber, the second opening aligned with a removable filter, the removable filter having a first surface facing the interior of the first chamber and a second surface opposite the first surface, the removable filter defining a plurality of pores configured to retain the one or more target cells from the fluid sample on the first surface and/or in the plurality of pores and to pass any non-target cells and fluid from the fluid sample through the plurality of pores, each pore of the plurality of pores having a first diameter in the first surface, the first diameter being smaller than a diameter of the one or more target cells, and a second diameter in the second surface, the second diameter being greater than the first diameter, the second surface of the removable filter being in contact with a hydrophilic microporous wick structure such that any non-target cells and the fluid from the fluid sample are drawn into a second chamber in communication with the first chamber through the plurality of pores; and removing the filter with the one or more target cells isolated on the first surface of the filter.

23. The method of claim 22, further comprising diluting the fluid sample prior to introducing the fluid sample into the first chamber.

24. The method of claim 22, further comprising selecting the filter based at least in part on a dimension of the one or more target cells.

25. The method of claim 22, further comprising inserting the filter between the first chamber and the second chamber.

26. The method of claim 22, further comprising introducing a wash into the first chamber after introducing the fluid sample into the first chamber but prior to removing the filter.

27. The method of claim 22, further comprising disposing of the hydrophilic microporous wick structure.

28. The method of claim 22, further comprising transferring the filter to at least one of a tissue culture vessel and a glass slide.

29. The method of claim 28, wherein the filter is transferred to the glass slide, the method further comprising ascertaining a presence and/or an absence of the one or more target cells on the first surface of the filter.

30. The method of claim 28, wherein the filter is transferred to the tissue culture vessel, the method further comprising culturing the one or more target cells on the first surface of the filter.

31. A kit for testing for isolating one or more target cells from a fluid sample, the kit comprising:
the apparatus of claim 1; and
a removable filter configured to retain any target cells in the fluid sample.

32. A kit for growing one or more target cells isolated from a fluid sample, the kit comprising:
the apparatus of claim 1;
a removable filter configured to retain and promote growth of any target cells in the fluid sample; and
a cell culture vessel configured to receive the removable filter and any culture media.

* * * * *